United States Patent [19]
Festal et al.

[11] Patent Number: 5,183,924
[45] Date of Patent: Feb. 2, 1993

[54] DERIVATIVES OF BENZOCYCLOALKENYLDIHYDROXYALKANOIC ACIDS, PROCESSES OF PREPARATION AND MEDICATIONS CONTAINING THEM

[75] Inventors: Didier Festal, Ecully; Jean-Yves Nioche, Limonest; Denis Descours, Villeurbanne; Robert Bellemin, Lyons; Jacques Decerprit, Neyron, all of France

[73] Assignee: Lipha, Lyonnaise Industrielle Pharmaceutique, Lyons, France

[21] Appl. No.: 782,195

[22] Filed: Oct. 24, 1991

Related U.S. Application Data

[62] Division of Ser. No. 469,121, Jan. 24, 1990, Pat. No. 5,082,859.

[30] Foreign Application Priority Data

Jan. 24, 1989 [FR] France ................................ 89 00790

[51] Int. Cl.$^5$ ............................................. C03C 69/76
[52] U.S. Cl. ........................................ 560/56; 560/45; 549/266; 549/270; 549/357; 549/359; 549/362; 562/451; 562/466; 564/163; 564/164; 564/165; 564/172
[58] Field of Search ............... 560/56, 45; 562/451, 562/466; 564/163, 164, 165, 172; 549/266, 270, 357, 359, 362

[56] References Cited
FOREIGN PATENT DOCUMENTS
2300148 12/1990 Japan .
1209857 10/1970 United Kingdom .

*Primary Examiner*—Paul J. Killos
*Attorney, Agent, or Firm*—Browdy and Neimark

[57] ABSTRACT

Derivatives of benzocycloalkenyldihydroxyalkanoic acids, inhibitors of HMG CoA reductase, antagonists of thromboxane $A_2$ receptors and antifungals, denoted by the formula I

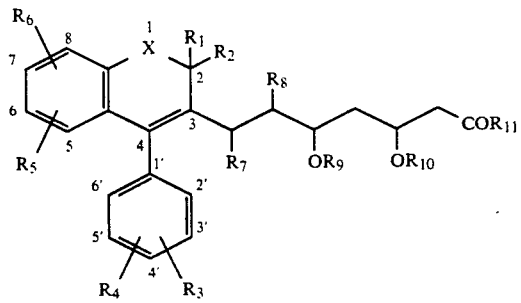

in which $X = CH_2$, O or S; $R_1$ and $R_2$, identical or different, $=H$, $C_{1-3}$ alkyl or together form a $—(CH_2)_n—$ chain ($n = 4,5$) optionally substituted symmetrically by one or two $C_{1-3}$ alkyl radicals.

$R_3$ and $R_4$, identical or different, $=H$, $CF_3$, halogen (Cl, F, Br), $C_{1-5}$N,N-dialkylamino, $C_{1-4}$ alkyl, $C_{1-5}$-alkoxy, $C_{1-3}$ alkylthio, or phenyl optionally substituted by at most substituents which may be identical or different and may denote $C_{1-3}$ alkyl or $C_{1-3}$ alkoxy radicals or halogens (F, Cl), it being understood that when one of $R_3$ and $R_4$ denotes the radicals: $CF_3$, N,N-dialkylamino, $C_6H_5$ or substituted phenyl, it is present at the vertices 3', R' or 5' according to formula 1 and the other denotes a hydrogen atom.

$R_5$ and $R_6$, (which may be identical or different) $=H$, halogen (F, Cl, Br), $CF_3$, $C_{1-3}$ alkoxy, $C_8H_5$, optionally substituted by at most two substituents which may be identical or different and may denote radicals: $C_{1-3}$ alkyl or $C_{1-3}$ alkoxy or halogen atoms (F, Cl), on condition that when one of $R_5$ and $R_6 = CF_3$, $C_6H_5$ or substituted phenyl, it is present at the vertex 6 or 7 and the other denotes a hydrogen atom.

The substituents $R_3$ and $R_4$ or $R_5$ and $R_6$ may also together form, on condition of being at two contiguous vertices, diradicals of formulae: $—CH=CH—CH=CH—$, $—(CH_2)_m—$ and $—O(CH_2)_pO—$, in which $m = 3$ or 4, $p = 1$ or 2, it being understood that when $R_3$ and $R_4$ or $R_5$ and $R_6$ form the chain sequence $—O(CH_2)_pO—$, the latter is linked to the vertices 3' and 4' and 5' or 6 and 7 according to the formula 1.

$R_7$ and $R_8 = H$ or, together with the existing C-C bond, form a double bond of trans geometry; $R_9$ and $R_{10} = H$ or together form a $C_{1-3}$ dialkylmethylene residue.

In the form of free acids, salts, esters, amides or δ-lactones.

Hypocholesterolaemiant, antithrombotic and antifungal medications containing them.

14 Claims, No Drawings

DERIVATIVES OF BENZOCYCLOALKENYLDIHYDROXYALK-ANOIC ACIDS, PROCESSES OF PREPARATION AND MEDICATIONS CONTAINING THEM

This is a division of Ser. No. 469,121, filed Jan. 24, 1990, now U.S. Pat. No. 5,082,859.

The present invention relates to new derivatives of benzocycloalkenyldihydroxyalkanoic acids, to processes for preparing these compounds and to pharmaceutical compositions containing them.

It is known that certain derivatives of 3,5-dihydroxy-3-methylpentanoic acid, known by the name of "mevalonic" acid, are inhibitors of the enzyme 3-hydroxy-3-methylglutaryl coenzyme A reductase, responsible for the biosynthesis of cholesterol, (cf. Singer et al., Proc. Sc. Exper. Biol. Med., 102, 275, 1959).

More recently, a compound derived from mevalonic acid, called "Lovastatine", formerly "Mevinoline", has been proposed as an active principle of medicinal compositions which can be employed in the treatment of hypercholesterolaemias, (cf. U.S. Pat. No. 4,231,938 in the name of the Merck Company).

It has now fortuitously been found that new derivatives of benzocycloalkenyldihydroxyalkanoic acids are endowed with hypocholesterolaemiant, antithrombotic and antifungal properties.

The invention relates more particularly to the compounds of formula 1, numbered to permit a better understanding of the invention and solely by way of example as shown,

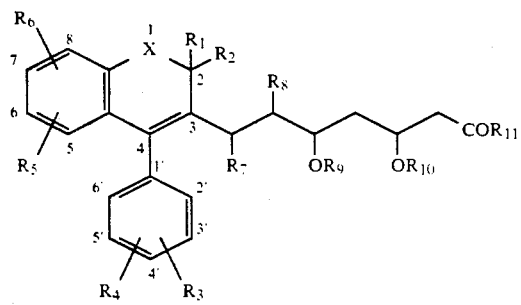

in which,

X denotes a —$CH_2$— methylene chain link, an oxygen atom or a sulphur atom.

$R_1$ and $R_2$, which may be identical or different, denote hydrogen atoms or alkyl radicals containing 1 to 3 carbon atoms. $R_1$ and $R_2$ may also together form an alkylene chain: —$(CH_2)_n$—, if appropriate substituted symmetrically by one or two alkyl radicals containing 1 to 3 carbon atoms and in which the number n of chain links may take the values 4 or 5.

$R_3$ and $R_4$, which may be identical or different, denote hydrogen atoms, halogen atoms (fluorine, chlorine or bromine), the radicals: trifluoromethyl, N,N-dialkylamino containing 1 to 3 carbon atoms, alkyl containing 1 to 4 carbon atoms, alkoxy containing 1 to 5 carbon atoms, alkylthio containing 1 to 3 carbon atoms, or phenyl optionally substituted by at most two substituents which may be identical or different and may denote the radicals: alkyl containing 1 to 3 carbon atoms, alkoxy containing 1 to 3 carbon atoms or halogen atoms (fluorine or chlorine), on condition that when one of the substituents $R_3$ and $R_4$ denotes the radicals: trifluoromethyl, N,N-dialkylamino, phenyl or substituted phenyl, it is present on the vertices 3', 4' or 5' (meta or para) according to formula 1 and the other substituent denotes a hydrogen atom.

$R_5$ and $R_6$, which may be identical or different, denote hydrogen atoms, halogen atoms (fluorine, chlorine or bromine), the radicals: trifluoromethyl, alkyl containing 1 to 3 carbon atoms, alkoxy containing 1 to 3 carbon atoms, or a phenyl radical, if appropriate substituted by at most two substituents which may be identical or different and may denote the radicals: alkyl containing 1 to 3 carbon atoms, alkoxy containing 1 to 3 carbon atoms, or halogens (chlorine or fluorine) on condition that when one of the substituents $R_5$ and $R_6$ denotes the radicals: trifluoromethyl, phenyl or substituted phenyl, it is present on the vertices 6 or 7 according to the formula 1 and the other substituent denotes a hydrogen atom.

The substituents $R_3$ and $R_4$ or $R_5$ and $R_6$ may also together form, on condition of being at two contiguous vertices, the diradicals: diethylene, alkylene or alkylenedioxy, of formulae: —CH=CH—CH=CH—, —$(CH_2)_m$—, and —$O(CH_2)_pO$— respectively, in which m may take the value 3 or 4 and p the value 1 or 2, and on condition that when $R_3$ and $R_4$ or $R_5$ and $R_6$ form an alkylenedioxy diradical, the latter is linked to the vertices 3' and 4' or 4' and 5' or the vertices 6 and 7, according to the formula 1.

Each of the substituents $R_7$ and $R_8$ denotes a hydrogen atom or, together and with the existing C—C bond, they form a double bond of trans (E) geometry.

Each of the substituents $R_9$ and $R_{10}$ denotes a hydrogen atom or together they form a dialkylmethylene residue containing 1 to 3 carbon atoms.

$R_{11}$ may denote a hydroxyl radical, in which case the compounds of formula 1 are carboxylic acids, in free form.

The compounds of formula 1 may also be obtained in the form of esters and amides, which also form part of the invention.

Those particularly preferred are the esters and amides, physiologically acceptable, of formula 1, in which the substituent $R_{11}$ denotes alkoxy radicals containing 1 to 4 carbon atoms, benzyloxy, alkylamino or N,N-dialkylamino containing 1 to 3 carbon atoms, imino containing 4 to 6 carbon atoms, cycloalkylamino containing 3 to 6 carbon atoms or the amino or benzylamino radicals.

Compounds of formula 1 in the form of salts, that is to say in whose formula the substituent $R_{11}$ denotes a residue of formula —$O^-M^+$ in which $M^+$ denotes a pharmaceutically acceptable cation, also form part of the invention; among these, those more particularly preferred are the sodium, potassium, magnesium and ammonium salts.

The compounds of formula 1 can exist in the form of δ-lactones when the substituent $R_{11}$ forms a single bond with the substituent $R_9$; compounds of formula 1 in δ-lactone form are also part of the invention.

According to a preferred form of the invention, the subject of the latter is compounds of formula 1 in which the substituents $R_1$ and $R_2$ are identical or form an unsubstituted alkylene chain: —$(CH_2)_n$— in which the number n of chain units is equal to 4 or 5.

A particular meaning of the substituents $R_1$ and $R_2$, when they denote alkyl radicals containing 1 to 3 carbon atoms, is, for example, methyl.

A particular value of n when the substituents $R_1$ and $R_2$ form a —$(CH_2)_n$— alkylene chain is, for example, 4.

Particular meanings in the case of either of the substituents $R_3$ and $R_4$ are, solely by way of example, when it denotes a halogen atom: fluorine or chlorine;

when it denotes an alkyl radical containing 1 to 4 carbon atoms: methyl or ethyl;

when it denotes an alkoxy radical containing 1 to 5 carbon atoms: methoxy or ethoxy;

when it denotes an alkylthio radical containing 1 to 3 carbon atoms: methylthio;

when it denotes a substituted phenyl radical: phenyl para-substituted by a fluorine atom or by a methyl or methoxy radical.

A particular value of m when the substituents $R_3$ and $R_4$ form a $—(CH_2)_m—$ diradical is, by way of example, 4.

A particular value of p when the substituents $R_3$ and $R_4$ form an $—O(CH_2)_pO—$ alkylenedioxy diradical is, for example, 1.

Particularly appropriate arrangements of the radicals $R_3$ and $R_4$ are produced, for example, when $R_3$ and $R_4$ denote alkyl radicals containing 1 to 4 carbon atoms and/or halogen atoms, or a halogen atom and an alkoxy radical containing 1 to 5 carbon atoms; when one of the substituents $R_3$ and $R_4$ is a halogen atom, or an alkyl radical containing 1 to 4 carbon atoms, or an alkoxy radical containing 1 to 5 carbon atoms, or an alkylthio radical containing 1 to 3 carbon atoms and the other denotes a hydrogen atom.

Appropriate specific arrangements of the radicals $R_3$ and $R_4$ are produced, for example, when they denote methyl radicals in position 3' and 5', a fluorine atom in position 4' and a methyl radical in position 3', fluorine atoms in position 3' and 4', a fluorine atom in position 3' or 4' and a hydrogen atom, a methyl or ethyl radical in position 4' and a hydrogen atom, a methoxy radical in position 3' or 4' and a hydrogen atom, a chlorine atom in position 3' or 4' and a hydrogen atom, or hydrogen atoms.

A particular meaning of either of substituents $R_5$ and $R_6$ is, by way of examples, when it denotes a halogen atom: fluorine or chlorine;

when it denotes an alkyl radical containing 1 to 3 carbon atoms: methyl;

when it denotes an alkoxy radical containing 1 to 3 carbon atoms: methoxy;

when it denotes a substituted phenyl radical: a phenyl radical para-substituted by a fluorine or chlorine atom or by a methoxy radical.

A particular value of m when the substituents $R_5$ and $R_6$ together form a $—(CH_2)_m—$ alkylene chain is, for example, the value 4.

A particular value of p when the substituents $R_5$ and $R_6$ together form an $—O(CH_2)_pO—$ alkylenedioxy chain is the value 1.

Particularly appropriate arrangements of the radicals $R_5$ and $R_6$ are produced, for example, when they denote halogen atoms (fluorine, chlorine, bromine) alkyl radicals containing 1 to 3 carbon atoms or alkoxy radicals containing 1 to 3 carbon atoms or when one of the substituents $R_5$ and $R_6$ denotes a halogen atom which may be fluorine, chlorine or bromine, or denotes an alkyl radical containing 1 to 3 carbon atoms or an alkoxy radical containing 1 to 3 carbon atoms and the other substituent denotes a hydrogen atom.

Specific appropriate arrangements of the radicals $R_5$ and $R_6$ are produced, for example, when they denote methyl radicals in positions 5 and 7, a chlorine atom in position 6 and a hydrogen atom, a methoxy radical in position 6 and a hydrogen atom, a fluorine atom in position 6 or 7 and a hydrogen atom, a methyl radical in position 6 or 7 and a hydrogen atom, a 4-fluorophenyl radical in position 6 or 7 and a hydrogen atom, or two hydrogen atoms.

A particular meaning of the substituents $R_9$ and $R_{10}$, when they form a dialkylmethylene residue, is, for example, dimethylmethylene.

Particular meanings of the substituent $R_{11}$ are, solely by way of example, when it denotes an alkoxy radical containing 1 to 4 carbon atoms: methoxy or ethoxy;

when it denotes an alkylamino radical containing 1 to 3 carbon atoms: methylamino, ethylamino or isopropylamino;

when it denotes an N,N-dialkylamino radical containing 1 to 3 carbon atoms: diethylamino;

when it denotes an imino radical containing 4 to 6 carbon atoms; pyrrolidino.

The compounds of formula 1 in which the substituents $R_7$ and $R_8$ form a bond together are preferred to the corresponding compounds of formula 1 in which each of the substituents $R_7$ and $R_8$ denotes a hydrogen atom.

Everything else being equal, the compounds of formula 1 in which each of the substituents $R_9$ and $R_{10}$ denotes a hydrogen atom are preferred to the compounds in which the substituents $R_9$ and $R_{10}$ form a dialkylmethylene residue.

Everything else being equal, the nonlactonic compounds of formula 1 are preferred to the $\delta$-lactonic compounds.

Among the nonlactonic compounds of formula 1, the esters, the amides and the salts are generally preferred to the free acids.

Everything else being equal, the erythro stereoisomers are preferred to the threo stereoisomers (the terms erythro and threo referring to the relative orientation of the $OR_9$ and $OR_{10}$ groups).

Among the $\delta$-lactonic compounds of formula 1, the trans stereoisomers are preferred to the cis stereoisomers (the terms cis and trans relating to the relative axial or equatorial positions of the two substituents of the $\delta$-lactone ring).

Specific groups of compounds of the invention which are particularly preferred comprise the compounds of formula 1 in which:

A) X denotes oxygen or sulphur atoms or a methylene chain link, each of $R_1$ and $R_2$ denotes a methyl radical or together they form a $—(CH_2)_4—$ tetramethylene chain, only one of the radicals $R_3$ and $R_4$ or $R_5$ and $R_6$ denotes a hydrogen atom, $R_7$ and $R_8$ together form a bond and each of $R_9$ and $R_{10}$ denotes a hydrogen atom.

B) X, $R_1$, $R_2$, $R_7$, $R_8$, $R_9$ and $R_{10}$ have the meanings given immediately above in A), one of the substituents $R_3$ and $R_4$ is a hydrogen atom and the other denotes a fluorine or chlorine atom, and only one of the substituents $R_5$ and $R_6$ denotes a hydrogen atom.

C) X, $R_1$, $R_2$, $R_7$, $R_8$, $R_9$ and $R_{10}$ have meanings which have just been defined above in A), one of the substituents $R_3$ and $R_4$ is a hydrogen atom and the other denotes a fluorine or chlorine atom, and each of the two substituents $R_5$ and $R_6$ denotes a hydrogen atom.

D) X, $R_1$, $R_2$, $R_7$, $R_8$, $R_9$ and $R_{10}$ have the particular meanings defined in A), the two substituents $R_3$ and $R_4$ are hydrogen atoms and only one of the radicals $R_5$ and $R_6$ denotes a hydrogen atom.

E) X, $R_3$, $R_4$, $R_5$, $R_6$, $R_7$, $R_8$, $R_9$ and $R_{10}$ have the meanings defined above in C) and $R_1$ and $R_2$ together form a $-(CH_2)_4-$ tetramethylene chain.

F) X, $R_1$, $R_2$, $R_7$, $R_8$, $R_9$ and $R_{10}$ have the meanings shown immediately above in E) and each of the substituents $R_3$, $R_4$, $R_5$ and $R_6$ denotes a hydrogen atom.

Each compound of formula 1 contains at least two centres of asymmetry which are the two carbon atoms carrying $OR_9$ and $OR_{10}$ residues when each of the substituents $R_9$ and $R_{10}$ denotes a hydrogen atom or they together form a dialkylmethylene residue or else which are the hydroxylated carbon and the tertiary carbon situated in a position alpha to the intracyclic oxygen atom when the substituents $R_9$ and $R_{11}$ together form a bond.

As a result of this, each compound, free acid, ester, amide, salt or δ-lactone, corresponding to the formula 1 can exist in the form of at least four stereoisomers in diastereoisomeric pairs, denoted by employing the usual configuration notations, R and S, by RR, SS, RS and SR or in the form of diastereoisomeric racemate mixtures, RR-SS and RS-SR.

All these stereoisomers also form part of the invention.

The compounds of formula 1 can contain more than two centres of asymmetry, especially when the substituents $R_1$ and $R_2$ are different, and this gives rise to additional stereoisomers, which also form part of the invention.

It is within a specialist's normal competence to isolate or to synthesize an optically active form of a compound of formula 1, for example by resolving a racemate or by synthesis starting with an optically active compound and to determine the biological properties of the isomers thus isolated according to the tests described hereinafter.

A physiologically acceptable ester and amide means an ester or an amide of a compound according to the invention which, when hydrolysed in physiological conditions, gives rise in such conditions to an alcohol or an amine which is physiologically acceptable, that is to say nontoxic in the desired doses.

The term "alkyl" means a linear or branched, saturated hydrocarbon chain sequence derived from the corresponding alkane by removal of a hydrogen atom.

The term "alkoxy" means an alkyl radical such as defined above, linked to the parent molecule via an oxygen atom.

The term "alkylamino" means a nitrogen atom substituted by a hydrogen atom and by an alkyl radical such as defined above, the free valency being employed to form the bond with the parent molecule.

The term "N,N-dialkylamino" means an alkylamino radical such as defined above in which the hydrogen atom is replaced by an alkyl radical such as defined above.

The term "imino" means a dialkylamino radical such as defined above, in which the two alkyl radicals together form an alkylene chain.

The expression "dialkyl . . . containing 1 to x carbon atoms" means that each of the two alkyl radicals making up the dialkyl residue may independently contain from 1 to x carbon atoms.

As specific compounds of the invention there may be mentioned, solely by way of examples, the following compounds whose structural formulae are given in the attached drawings:

Compound No. 1: (+,−)Ethyl 6E-erythro-7-(4-(4-fluorophenyl)-3-spiro(2,1'-cyclopentyl-2H-1-benzopyran))-3,5-dihydroxyhepten-6-oate.

Compound No. 2: (+,−)Methyl 6E-erythro-7-(1,2-dihydro-2,2-dimethyl-4-phenyl-3-naphthyl)-3,5-dihydroxyhept-6-enoate.

Compound No. 3: (+,−)Methyl 6E-erythro-7-(4-(4-chlorophenyl)-2,2-dimethyl-2H-benzothiapyran-3-yl)-3,5-dihydroxyhept-6-enoate.

Compound No. 4: (+,−)Ethyl erythro-7-(4-(4-fluorophenyl)-3-spiro(2,1'-cyclopentyl-2H-1-benzopyran))-3,5-dihydroxyheptanoate.

Compound No. 5: (+,−)Sodium 6E-erythro-7-(4-(4-fluorophenyl)-3-spiro(2,1'-cyclopentyl-2H-1-benzopyran))-3,5-dihydroxyhept-6-enoate.

Compound No. 6: (+,−)Benzyl 6E-erythro-7-(4-(4-fluorophenyl)-3-spiro(2,1'-cyclopentyl-2H-1-benzopyran))-3,5-dihydroxyhept-6-enoate.

Compound No. 7: (+,−)-6E-erythro-7-(4-(4-Fluorophenyl)-3-spiro(2,1'-cyclopentyl-2H-1-benzopyran))-3,5-dihydroxy-N-methylhept-6-enamide.

Compound No. 8: (+,−)-trans-6-(1E-2-(4-(4-Fluorophenyl)-3-spiro(2,1'-cyclopentyl-2H-1-benzopyran))-ethenyl)-4-hydroxy-3,4,5,6-tetrahydropyran-2-one.

Compound No. 9: (+,−)-trans-4-Hydroxy-3,4,5,6-tetrahydro6-(2-(4-(4-fluorophenyl))-3-spiro(2,1'-cyclopentyl-2H-1-benzopyran))ethyl)pyran-2-one.

Compound No. 10: (+,−)Sodium erythro-7-(4-(4-fluorophenyl)-3-spiro(2,1'-cyclopentyl-2H-1-benzopyran-))- 3,5-dihydroxyheptanoate.

Compound No. 11: (+,−)Ethyl (6-(1E-2-(-4-(4-fluorophenyl)-3-spiro(2,1'-cyclopentyl-2H-1-benzopyran))ethenyl)-2,2-dimethyl-1,3-dioxan-4-yl)acetate.

Compound No. 12: (+,−)Ethyl 6E-erythro-3,5-dihydroxy-7-(4-phenyl-3-spiro(2,1'-cyclopentyl-2H-1-benzopyran))hept-6-enoate.

Compound No. 13: (+,−)Ethyl 6E-erythro-7-(4-4-ethylphenyl)-3-spiro(2,1'-cyclopentyl-2H-1-benzopyran))-3,5-dihydroxyhept-6-enoate.

Compound No. 14: (+,−)Ethyl 6E-erythro-3,5-dihydroxy-7-(6-methyl-4-phenyl-3-spiro(2,1'-cyclopentyl-2H-1-benzopyran)hept-6-enoate.

Compound No. 15: (+,−)Methyl 6E-erythro-7-(7-fluoro-4-phenyl-3-spiro(2,1'-cyclopentyl-2H-1-benzopyran))-3,5-dihydroxyhept--6-enoate.

Compound No. 16: (+,−)Ethyl 6E-erythro-3,5-dihydroxy-7-(4-(4-methylphenyl)-3-spiro(2,1'-cyclopentyl-2H-1-benzopyran))hept-6-enoate.

Compound No. 17: (+,−)Ethyl 6E-erythro-7-(4-(3-fluorophenyl)-3-spiro(2,1'-cyclopentyl-2H-1-benzopyran))-3,5-dihydroxyhept-6-enoate.

Compound No. 18: (+,−)Ethyl 6E-erythro-3,5-dihydroxy-7-(4-(4-methoxyphenyl)-3-spiro(2,1'-cyclopentyl-2H-1-benzopyran))hept-6-enoate.

Compound No. 19: (+,−)Ethyl 6E-erythro-7-(4-(4-chlorophenyl)-3-spiro(2,1'-cyclopentyl-2H-1-benzopyran))-3,5-dihydroxyhept-6-enoate.

Compound No. 20: (+,−)Ethyl 6E-erythro-3,5-dihydroxy-7-(4-(1-naphthyl)-3-spiro(2,1'-cyclopentyl-2H-1-benzopyran))hept-6-enoate.

Compound 21: (+,−)Ethyl 6E-erythro-3,5-dihydroxy-7-(4-(3,5-dimethylphenyl)-3-spiro(2,1'-cyclopentyl-2H-1-benzopyran))hept-6-enoate.

Compound No. 22: (+,−)Methyl 6E-erythro-7-(4-(4-fluorophenyl)-5,7-dimethyl-3-spiro(2,1'-cyclopentyl-2H-1-benzopyran))-3,5-dihydroxyhept-6-enoate.

Compound No. 23: (+,−)Methyl 6E-erythro-7-(4-(4-ethoxyphenyl)-3-spiro(2,1'-cyclopentyl-2H-1-benzopyran))- 3,5-dihydroxyhept-6-enoate.

Compound No. 24: (+,−)Methyl 6E-erythro-3,5-dihydroxy-7-(4-(4-isopropyloxyphenyl)-3-spiro(2,1'-cyclopentyl-2H-1-benzopyran)hept-6-enoate.

Compound No. 25: (+,−)Methyl 6E-erythro-7-(4-(4-fluorophenyl)-6-methoxy-3-spiro(2,1'-cyclopentyl-2H-1-benzopyran))-3,5-dihydroxyhept-6-enoate.

Compound No. 26: (+,−)Methyl 6E-erythro-7-(4-(4-trifluoromethylphenyl)-3-spiro(2,1'-cyclopentyl-2H-1-benzopyran))-3,5-dihydroxyhept-6-enoate.

Compound No. 27: (+,−)Methyl 6E-erythro-3,5-dihydroxy-7-(4-(4-n-pentyloxyphenyl)-3-spiro(2,1'-cyclopentyl-2H-1-benzopyran))hept-6-enoate.

Compound No. 28: (+,−)Methyl 6E-erythro-7-(4-(4fluorophenyl)-3-spiro(2,1'-cyclopentyl-2H-1-naphtho(b)pyran))-3,5-dihydroxyhept-6-enoate.

Compound No. 29: (+,−)Methyl 6E-erythro-3,5-dihydroxy-7-(4-(4-methylthiophenyl)-3-spiro(2,1'-cyclopentyl-2H-1-benzopyran))hept-6-enoate.

Compound No. 30: (+,−)Ethyl 6E-erythro-7-(4-(4-tert-butylphenyl)-3-spiro(2,1'-cyclopentyl-2H-1-benzopyran)-3,5-dihydroxyhept-6-enoate.

Compound No. 31: (+,−)Ethyl 6E-erythro-7-(4-(4-fluorophenyl)-3-spiro(2,1'-cyclohexyl-2H-1-benzopyran))-3,5-dihydroxyhept-6-enoate.

Compound No. 32: (+,−)Methyl 6E-erythro-7-(4-(4-fluorophenyl)-7-isopropyloxy-3-spiro(2,1'-cyclopentyl-2H-1-benzopyran))-3,5-dihydroxyhept-6-enoate.

Compound No. 33: (+,−)-6E-erythro-7-(4-(4-Fluorophenyl)-3-spiro(2,1'-cyclopentyl-2H-1-benzopyran))-3,5-dihydroxyhept-6-enamide.

Compound No. 34: (+,−)-6E-erythro-7-(4-(4-Fluorophenyl)-3-spiro(2,1'-cyclopentyl-2H-1-benzopyran))-3,5-dihydroxy-N-isopropylhept-6-enamide.

Compound No. 35: (+,−)-6E-erythro-7-(4-(1,1'-Biphenyl-4-yl)-3-spiro(2,1'-cyclopentyl-2H-1-benzopyran))-3,5-dihydroxy-N,N-tetramethylenehept-6-enamide.

Compound No. 36: (+,−)-6E-erythro-7-(4-(4-Fluorophenyl)-3-spiro(2,1'-cyclopentyl-2H-1-benzopyran))-3,5 -dihydroxy-N-cyclohexylhept-6-enamide.

Compound No. 37: (+,−)-6E-erythro-N-Benzyl-7-(4-(4-fluorophenyl)-3-spiro(2,1'-cyclopentyl-2H-1-benzopyran))-3,5-dihydroxyhept-6-enamide.

Compound No. 38: (+,−)Sodium 6E-erythro-7-(4-(4-ethylphenyl)-3-spiro(2,1'-cyclopentyl-2H-1-benzopyran))-3,5-dihydroxyhept-6-enoate.

Compound No. 39: (+,−)Sodium 6E-erythro-3,5-dihydroxy-7-(6-methyl-4-phenyl-3-spiro(2,1'-cyclopentyl-2H-1-benzopyran))hept-6-enoate.

Compound No. 40: (+,−)Sodium 6E-erythro-3,5-dihydroxy-7-(4-(4-isopropylphenyl)-3-spiro(2,1'-cyclopentyl-2H-1-benzopyran))hept-6-enoate.

Compound No. 41: (+,−)Sodium 6E-erythro-3,5-dihydroxy-7-(4-phenyl-3-spiro(2,1'-cyclopentyl-2H-1-benzopyran))hept-6-enoate.

Compound No. 42: (+,−)Sodium 6E-erythro-7-(4-(4-chlorophenyl)-3-spiro(2,1'-cyclopentyl-2H-1-benzopyran))-3,5-dihydroxyhept-6-enoate.

Compound No. 43: (+,−)Ethyl 6E-erythro-3,5-dihydroxy-7-(4-phenyl-2H-1-benzopyran-3-yl)hept-6-enoate.

Compound No. 44: (+,−)Methyl 6E-erythro-7-(4-(4-fluorophenyl)-2,2-dimethyl-2H-1-benzopyran-3-yl)-3,5-dihydroxyhept-6-enoate.

Compound No. 45: (+,−)Ethyl 6E-erythro-7-(4-(4-fluorophenyl)-2-isopropyl-2H-1-benzopyran-3-yl)-3,5-dihydroxyhept-6-enoate.

Compound No. 46: (+,−)-trans-4-Hydroxy-3,4,5,6-tetrahydro-6-(1E-4-phenyl-3-spiro(2,1'-cyclopentyl-2H-1-benzopyran))ethenyl)-2H-pyran-2-one.

Compound No. 47: (+,−)-trans-6-(1E-2-(4-(4-Fluorophenyl)-6-methoxy-3-spiro(2,1'-cyclopentyl-2H-1-benzopyran))ethenyl)-4-hydroxy-3,4,5,6-tetrahydro-2H-pyran-2-one.

Compound No. 48: (+,−)-trans-6-(1E-2-(1,2-Dihydro-2,2-dimethyl-4-phenyl-3-naphthyl)ethenyl)-4-hydroxy-3,4,5,6-tetrahydro-2H-pyran-2-one.

Compound No. 49: (+,−)-trans-4-Hydroxy-3,4,5,6-tetrahydro-6-(1E-2-(2H-2,2-dimethyl-4-phenyl-3-benzothiapyranyl)ethenyl)- 2H-pyran-2-one.

Compound No. 50: (+,−)Methyl 6E-erythro-3,5-dihydroxy-7-(4-phenyl-3-spiro(2,1'-cyclopentyl-1,2-dihydronaphthalene))hept-6-enoate.

Compound No. 51: (+,−)Methyl 6E-erythro-7-(4-(4-fluorophenyl)-1,2-dihydro-2,2-dimethyl-3-naphthyl)-3,5-dihydroxyhept-6-enoate.

Compound No. 52: (+,−)Methyl 6E-erythro-7-(1,2-dihydro-2,2-dimethyl-4-phenyl-3-naphthyl)-3,5-dihydroxyhept-6-enoate.

Compound No. 53: (+,−)Methyl 6E-erythro-7-(4-(4-fluorophenyl)-3-spiro(2,1'-cyclopentyl-1,2-dihydronaphthalene))-3,5-dihydroxyhept-6-enoate.

Compound No. 54: (+,−)Methyl 6E-erythro-7-(4-(4-chlorophenyl)-3-spiro(2,1'-cyclopentyl-1,2-dihydronaphthalene))-3,5-dihydroxyhept-6-enoate.

Compound No. 55: (+,−)Methyl 6E-erythro-7-(4-(4-chlorophenyl)-1,2-dihydro-2,2-dimethyl-3-naphthyl)-3,5-dihydroxyhept-6-enoate.

Compound No. 56: (+,−)Methyl 6E-erythro-7-(4-(3-fluorophenyl)-3-spiro(2,1'-cyclopentyl-1,2-dihydronaphthalene))-3,5-dihydroxyhept-6-enoate.

Compound No. 57: (+,−)Sodium 6E-erythro-7-(4-(4-fluorophenyl)-1,2-dihydro-3-naphthyl)-3,5-dihydroxyhept-6-enoate.

Compound No. 58: (+,−)Methyl 6E-erythro-7-(1,2-dihydro-2-isopropyl-4-phenyl-3-naphthyl)-3,5-dihydroxyhept-6-enoate.

Compound No. 59: (+,−)Methyl 6E-erythro-7-(1,2-dihydro-2-methyl-4-phenyl-3-naphthyl)-3,5-dihydroxyhept-6-enoate.

Compound No. 60: (+,−)Methyl 6E-erythro-3,5-dihydroxy-7-(8-methyl-4-(4-methylphenyl)-3-spiro(2,1'-cyclopentyl-1,2-dihydronaphthalene))hept-6-enoate.

Compound No. 61: (+,−)Methyl 6E-erythro-7-(6-chloro-4-(4-chlorophenyl)-3-spiro(2,1'-cyclopentyl-1,2-dihydronaphthalene))-3,5-dihydroxyhept-6-enoate.

Compound No. 62: (+,−)Methyl 6E-erythro-3,5-dihydroxy-7-(8-methyl-4-(4-methoxyphenyl)-3-spiro(2,1' -cyclopentyl-1,2-dihydroxynaphthalene))-hept-6-enoate.

Compound No. 63: (+,−)Methyl 6E-erythro-7-(6-chloro-4-(4-fluorophenyl)-3-spiro(2,1'-cyclopentyl-1,2-dihydronaphthalene))-3,5-dihydroxyhept-6-enoate.

Compound No. 64: (+,−)Methyl 6E-erythro-7-(1,2-dihydro-2,2-dimethyl-7-methoxy-3-naphthyl)-3,5-dihydroxyhept-6-enoate.

Compound No. 65: (+,−)Sodium 6E-erythro-3,5-dihydroxy-7-(4-phenyl-3-spiro(2,1'-cyclopentyl-2H-1-benzothiapyran))hept-6-enoate.

Compound No. 66: (+,−)Methyl 6E-erythro-3,5-dihydroxy-7-(4-(4-methylphenyl)-3-spiro(2,1'-cyclopentyl-2H-1-benzothiapyran))hept-6-enoate.

Compound No. 67: (+,−)Methyl 6E-erythro-3,5-dihydroxy-7-(4-phenyl-2,2-dimethyl-3-2H-benzothiapyranyl)hept-6-enoate.

Compound No. 68: (+,−)Sodium 6E-erythro-3,5-dihydroxy-7-(4-phenyl-2,2-dimethyl-3-2H-benzothiapyranyl)hept-6-enoate.

The invention also relates to the processes for the preparation the compounds according to the invention, which are characterized in that they comprise at least, a) the reduction of a keto-ester of general formula 4, in which X, $R_1$, $R_2$, $R_3$, $R_4$, $R_5$, $R_6$, $R_7$, $R_8$ and $R_{11}$ have the general or particular meanings already defined,

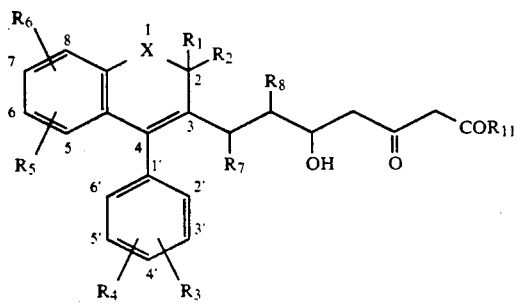

and, if appropriate, b) the transesterification of compounds of formula 1 or the alcoholysis of compounds of formula 1 in δ-lactone form or else the alkylation of compounds of formula 1 in the form of salts, c) the hydrolysis of compounds of formula 1 in ester or δ-lactone form, d) when $R_7$ and $R_8$ or $R_9$ and $R_{11}$ together form a single bond: the treatment of the corresponding compounds of formula 1 in the form of salts with a tertiary chloroamine, e) when $R_7$, $R_8$ and $R_{10}$ denote a hydrogen atom and $R_9$ and $R_{11}$ together form a bond: the catalytic reduction of the δ-lactonic compounds of formula 1 in which $R_7$ and $R_8$ form a bond or the lactonization of the corresponding acidic compounds of formula 1 in which $R_7$, $R_8$ and $R_{10}$ denote a hydrogen atom, f) the aminolysis of the compounds of formula 1 in ester or δ-lactone form, g) when $R_9$ and $R_{10}$ together form a dialkylmethylene residue: the cyclization of the corresponding compounds of formula 1 in which each of $R_9$ and $R_{10}$ denotes a hydrogen atom, using an alkoxyalkene.

The compounds of formula 1 in which X, $R_1$, $R_2$, $R_3$, $R_4$, $R_5$, $R_6$, $R_7$ and $R_8$ have the general or particular meanings defined previously and in which each of the substituents $R_9$ and $R_{10}$ denotes a hydrogen atom may be prepared, in ester form, by the reaction sequence illustrated by the following scheme I,

SCHEME I

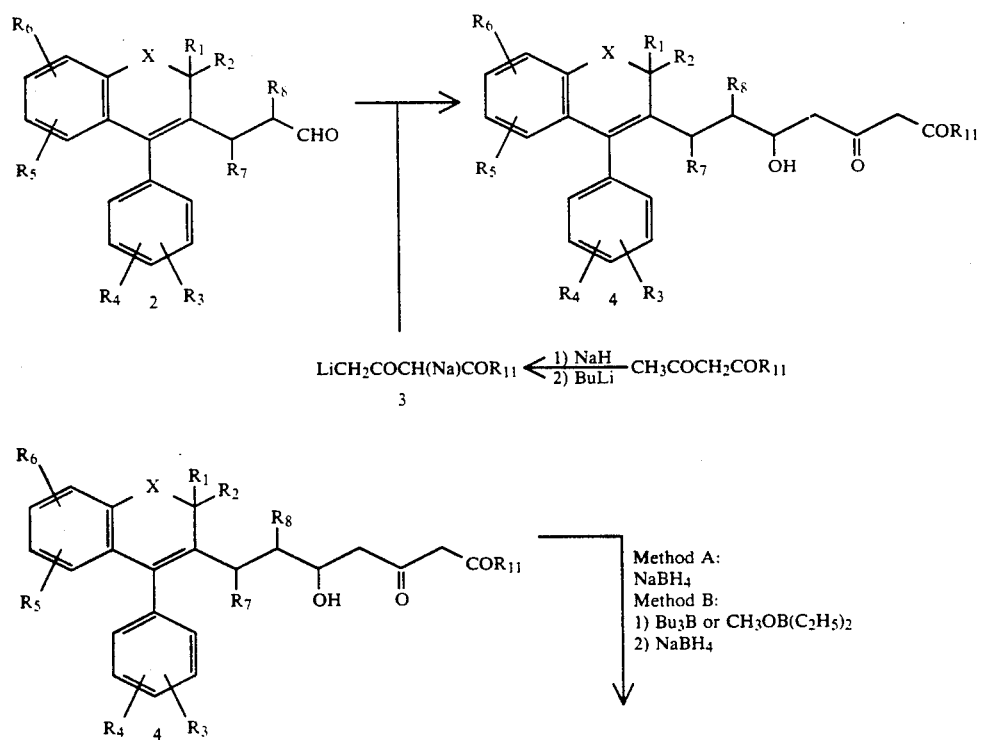

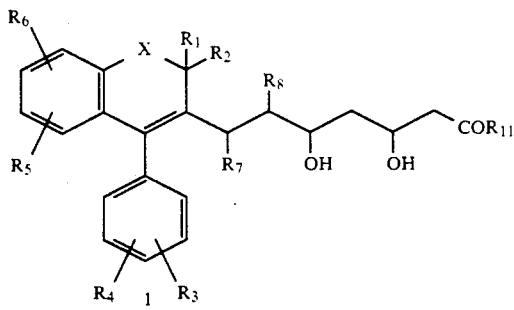

As shown in scheme I, the aldehyde compounds of formula 2 in which the substituents $R_1$, $R_2$, $R_3$, $R_4$, $R_5$, $R_6$, $R_7$ and $R_8$ have the particular or general meanings already defined are subjected to an aldol condensation with the appropriate acetoacetate in the form of mixed sodium and lithium double salt of formula 3 in which $R_{11}$ has the general or particular meanings already defined, in a polar solvent such as THF (cf. Kraus et al., J. Org. Chem., 48, 2111, 1983), to give the 7-substituted 5-hydroxy-3-oxohept-6-enoates of formula 4.

The esters 4, in solution in an inert solvent, such as THF or ether, and treated with an alkali metal borohydride, preferably sodium borohydride (method A) lead to the compounds 1 in the form of a mixture of threo and erythro isomers, which can be separated by the usual physicochemical methods such as, for example, chromatography.

An alternative (method B), preferred to method A in that it gives the compounds according to the invention in erythro form, consists in treating the esters 4 in solution in an appropriate solvent such as THF, before the reduction with an alkali metal borohydride, with a complexing agent, preferably a trialkylborane like tributylborane (cf. Narasaka, Chem. Letters, 1415-1418, 1980) or an alkoxydialkylborane like methoxydiethylborane (cf. Chen et al., Tetrahed. Lett. 28 (2), 155-158, 1987).

The compounds of formula 2 in which the substituents $R_7$ and $R_8$ together form a bond may be prepared according to the reaction sequence illustrated by the following scheme II,

SCHEME II

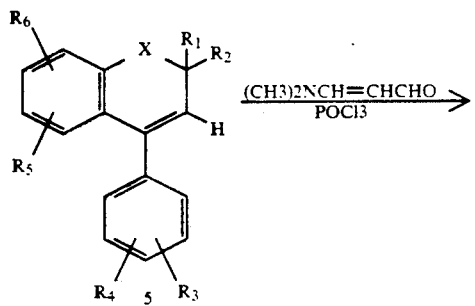

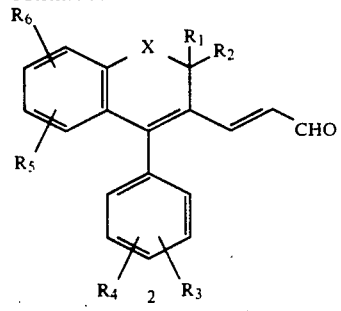

As shown in scheme II, the compounds of formula 5 in which X, $R_1$, $R_2$, $R_3$, $R_4$, $R_5$ and $R_6$ have the general or particular meanings already defined are subjected to a Vilsmeier reaction with N,N-dimethyl-3-aminoacrolein (cf. Ullrich and Breitmaier, Synthesis 8, 641-645, 1983), in an inert solvent like acetonitrile and at a temperature of between 20° C. and the reflux temperature, to give the compounds 2 of trans geometry, as shown by NMR spectroscopy.

Another process for preparing the aldehydes of formula 2 in which $R_7$ and $R_8$ together form a bond is illustrated by the following scheme III,

SCHEME III

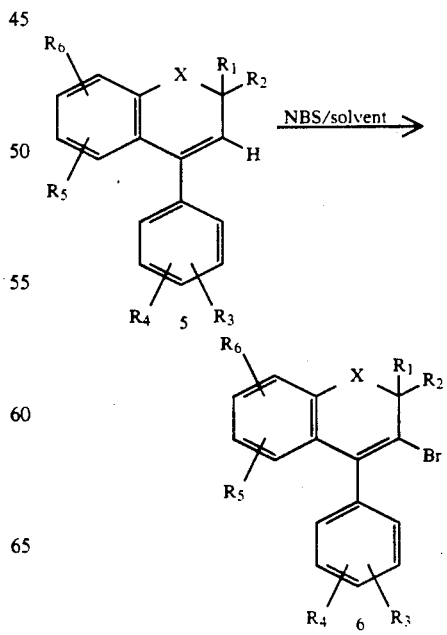

-continued

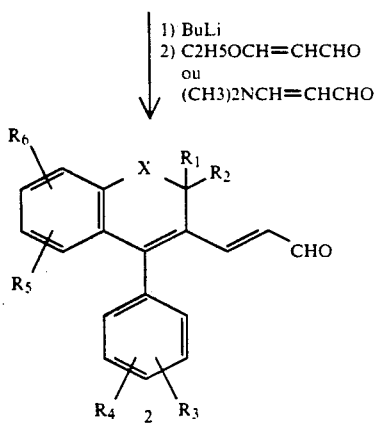

As shown in scheme III, the compounds of formula 5 are subjected to a bromination reaction with N-bromosuccinimide (NBS) in N,N-dimethylformamide (DMF) or in a chlorinated solvent like carbon tetrachloride or methylene chloride, to produce the corresponding 3-bromo compounds 6, which are successively treated with butyllithium in a suitable solvent, preferably an ether like, for example, diethyl ether and then with 3-ethoxyacrolein or N,N-dimethyl-3-aminoacrolein to form the aldehydes 2 in trans form as shown by NMR spectroscopy.

An alternative for preparing the aldehyde intermediates of formula 2 in which $R_7$ and $R_8$ together form a bond is illustrated by the following scheme IV,

SCHEME IV

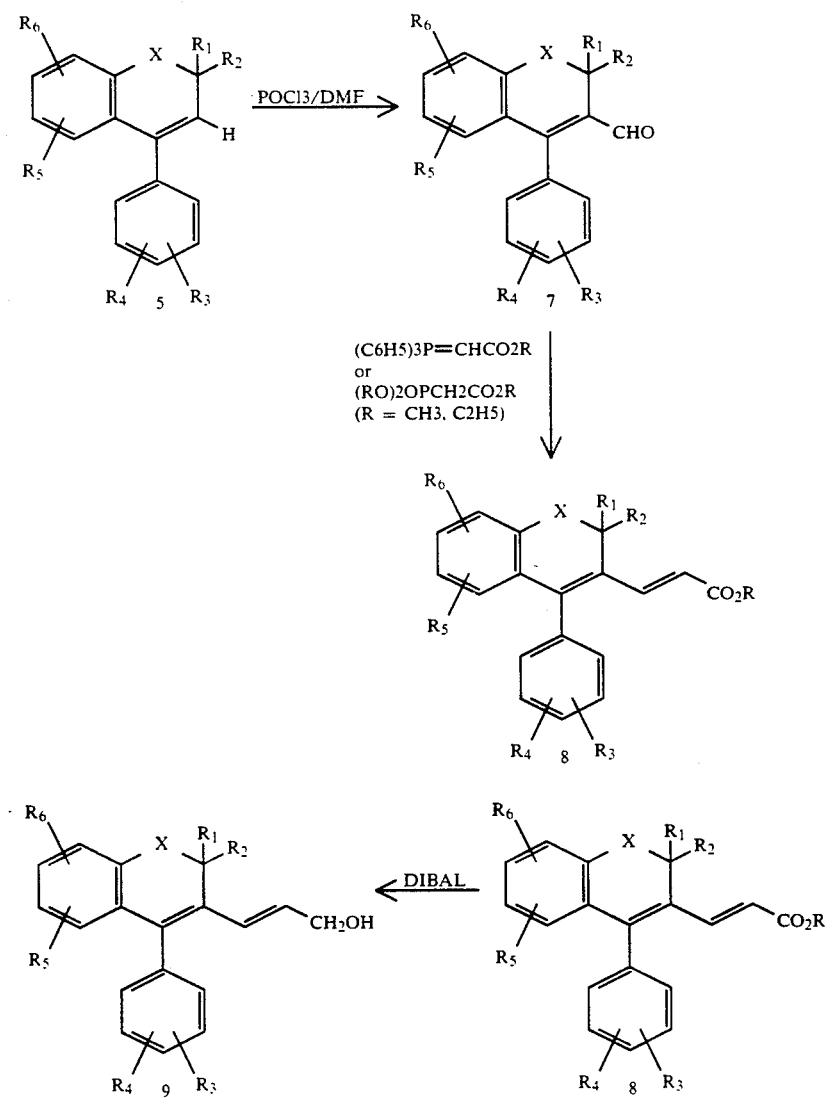

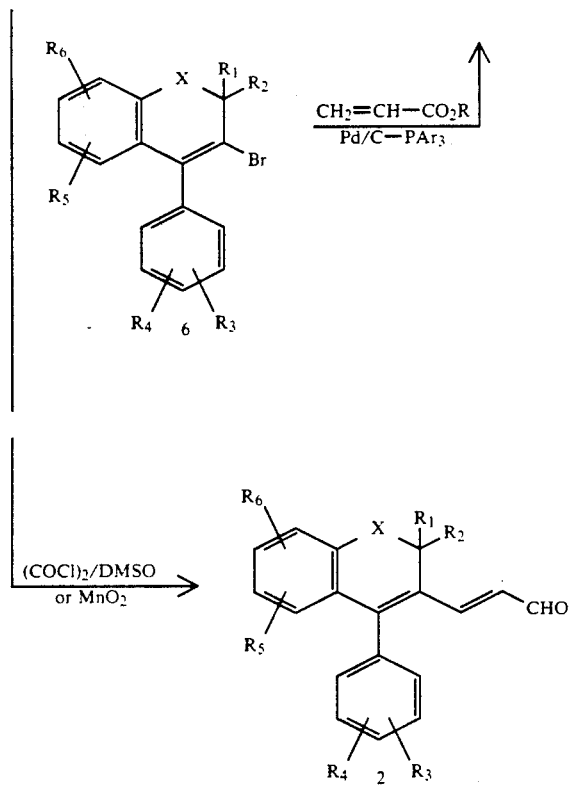

As shown in scheme IV, the compounds of formula 5 are subjected to a Vilsmeier reaction with N,N-dimethylformamide (cf. Jackson et al., J. Am. Chem. Soc. 103, 533, 1981) in an inert solvent to form the corresponding aldehydes 7, which are subjected to a Wittig reaction with ethoxy- or methoxycarbonylmethylenetriphenylphosphorane, or with a methyl or ethyl phosphonoacetate (cf. Organic Reactions, 14, 273, 1965) to give the 3-substituted propenoic esters 8 whose geometry is trans, as shown by NMR spectroscopy.

An alternative for preparing the intermediate compounds of formula 8, which is particularly preferred when X denotes a sulphur atom, consists in reacting a bromo compound of formula 6 with an alkyl acrylate, preferably methyl or ethyl acrylate in the presence of a basic agent such as triethylamine or sodium bicarbonate, of palladium dispersed on charcoal or of a derivative of palladium such as palladium dichloride or its acetate and of a ligand, preferably a triarylphosphine like, for example, tri-ortho-tolylphosphine in a suitable solvent like N,N-dimethylformamide.

The esters 8 are reduced, with diisobutylaluminium hydride (DIBAL) in a solvent, generally diethyl ether or THF, to the corresponding 3-substituted trans propenols 8, which are then subjected to a controlled oxidation with oxalyl chloride in DMSO (cf. Swern et al., J. Org. Chem., 43, 2480, 1978) or with manganese dioxide in a suitable solvent like, for example, THF, to give the aldehydes of formula 2 of trans geometry.

The aldehydes of formula 2 in which each of the substituents $R_7$ and $R_8$ denotes a hydrogen atom can be prepared according to the reaction sequence illustrated by the following scheme V,

SCHEME V

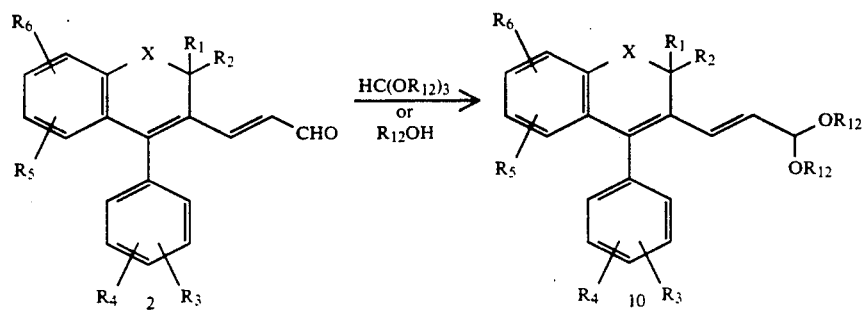

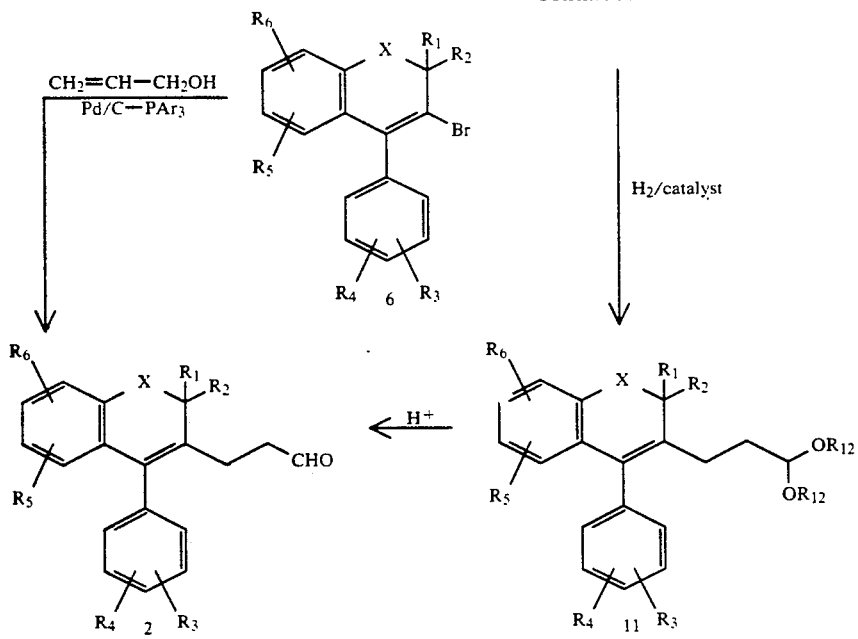

SCHEME VI

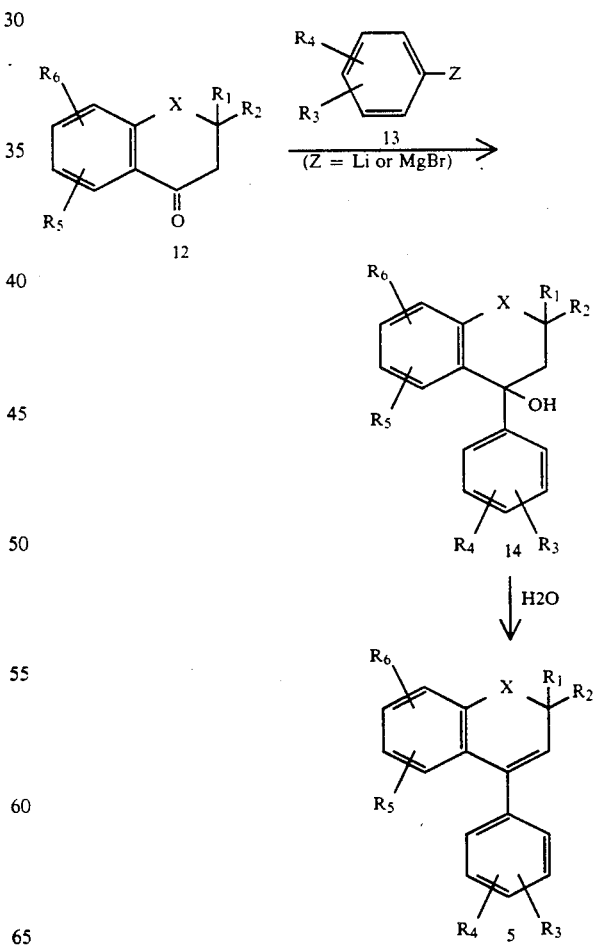

According to the reaction sequence of scheme V, the aldehydes of formula 2 where $R_7$ and $R_8$ form a double bond are subjected to an acetalization reaction, for example with an orthoformate of formula $HC(OR_{12})_3$ in which $R_{12}$ denotes an alkyl radical containing 1 to 4 carbon atoms, preferably methyl or ethyl, in the presence of an acidic resin or else to an acid-catalysed reaction with an alcohol of formula $R_{12}OH$ in which $R_{12}$ has the above meanings or may denote a radical of formula —$(CH_2)_qOH$, in which q=2 or 3, to form the compounds 10; the methylene radical —$R_{12}$ ... $R_{12}$— then forms a 5 or 6-membered ring with the oxygen atoms to which it is attached.

The compounds 10 are then hydrogenated, preferably at low pressure and in the presence of a metal catalyst like, for example, palladium dispersed on charcoal, in an appropriate solvent like, for example, THF or an alcohol like methanol, to the acetals of the corresponding 3-substituted propanaldehydes 11, which can then be deacetalized to the propanaldehydes 2 by the usual deacetalization methods which include, for example, the treatment of the acetal with an acidic resin in an acetone-water mixture, or more generally with an acidic catalyst, in a solvent or mixture of appropriate solvents.

An alternative for preparing the aldehyde compounds of formula 2 in which each of the substituents $R_7$ and $R_8$ denotes a hydrogen atom consists in reacting the bromo compounds of formula 6 with allyl alcohol in the presence of a basic agent such as triethylamine or sodium bicarbonate, of palladium dispersed on charcoal or a derivative of palladium such as palladium dichloride or its acetate and of a ligand, preferably a triarylphosphine like, for example, tri-ortho-tolylphosphine in a suitable solvent like N,N-dimethylformamide.

The compounds of formula 5 may be prepared according to the sequence illustrated by the following scheme VI, according to which the ketonic compounds of formula 12 in which X, $R_1$, $R_2$, $R_5$ and $R_6$ have the particular or general meanings already defined are treated with the appropriate lithium or magnesium compound of formula 13, in which $R_3$ and $R_4$ have the general or particular meanings defined previously, to give, by 1-2 addition, the corresponding alcohols 14, which are dehydrated to the desired compounds 5 by the action of a dehydrating agent such as potassium hydrogen sulphate or else para-toluenesulphonic acid.

The compounds of formula 12 in which X denotes oxygen and sulphur atoms and $R_1$, $R_2$, $R_5$ and $R_6$ have the general or particular meanings defined previously are prepared according to the process of Kabbe et al., Synthesis, 12, 886, 1978.

The compounds of formula 12 in which X denotes a methylene chain link and $R_1$, $R_2$, $R_5$ and $R_6$ have the general or particularly meanings stated above are prepared according to the sequence of reactions which is illustrated by the following scheme VII,

SCHEME VII

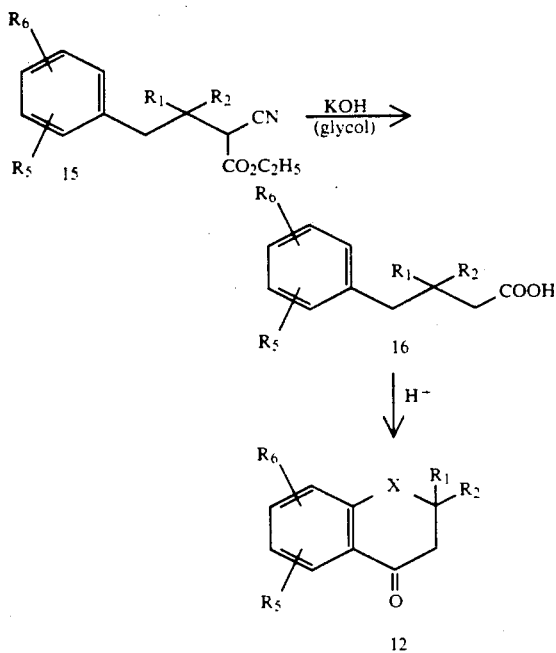

As shown by scheme VII, the cyanoesters of formula 15, in which $R_1$, $R_2$, $R_5$ and $R_6$ have the general or particular meanings already defined are hydrolysed and decarboxylated by glycolic potassium hydroxide to the corresponding acids 16 which are cyclized to the compounds 12 by heating in an acidic medium. The compounds of formula 15 are prepared according to the process described by Prout et al., Org. Synth., Coll. vol. IV, 93, 1963.

The compounds of formula 1 in ester form can also be prepared by transesterification of compounds of formula 1 which differ in the substituent $R_{11}$ or else by alcoholysis of compounds of formula 1 in δ-lactone form, or else by O-alkylation of the compounds of formula 1 in the form of salts, preferably sodium salts, with a bromide or an iodide of formula $R_{11}$-Br(I) in which $R_{11}$ has the general or particular meanings defined previously.

The esters corresponding to the formula 1 in which each of the substituents $R_7$ and $R_8$ denotes a hydrogen atom can also be prepared by hydrogenation of the corresponding esters of formula 1 in which the substituents $R_7$ and $R_8$ form a bond, preferably at low pressure, in the presence of a metal catalyst like palladium or platinum oxide in an appropriate solvent like, for example, THF.

The compounds of formula 1 in the form of salts can be prepared by basic hydrolysis, for example, with sodium hydroxide or potassium hydroxide, in a suitable solvent, preferably an alcohol, of the corresponding compounds of formula 1 in ester form, preferably the methyl or ethyl esters, or else in δ-lactone form.

The δ-lactonic compounds of formula 1 in which the substituents $R_7$ and $R_8$ together form a bond can be prepared by reacting the corresponding compounds of formula 1 in the form of salts, preferably sodium salts, with a chloroamine, preferably 2-chloroethyl-N,N-diethylamine in an appropriate, preferably carbonyl-containing, solvent like acetone or butanone.

The δ-lactonic compounds of formula 1 in which each of $R_7$, $R_8$ and $R_{10}$ denotes a hydrogen atom are prepared by lactonization of the corresponding acids of formula 1, that is to say in whose formula $R_{11}$ denotes a hydroxyl radical: the lactonization reaction is preferably carried out by heating the acids in an inert aromatic solvent such as benzene, toluene, xylene or a mixture thereof, if appropriate in the presence of a dehydrating agent like, for example, para-toluenesulphonic acid; another highly valued process for preparing the δ-lactonic compounds of formula 1 in which $R_7$, $R_8$ and $R_{10}$ denote a hydrogen atom consists in hydrogenating, in heterogeneous phase, the corresponding unsaturated compounds of formula 1, that is to say in whose formula $R_7$ and $R_8$, or $R_9$ and $R_{11}$, together form a bond, in the presence of a metal catalyst, preferably palladium dispersed on charcoal or else platinum oxide, in an appropriate solvent, preferably an ether like THF or an alcohol like methanol or ethanol.

The acidic compounds of formula 1 in which each of $R_9$ and $R_{10}$ denotes a hydrogen atom may be prepared by acidification of the corresponding compounds of formula 1 in the form of salts or else by hydrogenolysis, in the presence of palladium dispersed on carbon, of the corresponding benzyl esters, that is to say compounds of formula 1 in which $R_{11}$ denotes a benzyloxy residue.

The compounds of formula 1 in amide form are prepared by aminolysis with an excess of amine in a polar solvent, preferably methanol or ethanol, of the corresponding esters of formula 1, preferably the methyl or ethyl esters, or of the corresponding compounds of formula 1 in δ-lactone form.

The compounds of formula 1 in which the substituents $R_9$ and $R_{10}$ together form a $C_{1-3}$ dialkylmethylene group are prepared by reaction of the corresponding compounds of formula 1 in which each of $R_9$ and $R_{10}$ denotes a hydrogen atom with the appropriate alkoxyalkene (the term alkoxyalkene denoting an alkene containing 3 to 7 carbon atoms, substituted on the double bond by an alkoxy radical such as defined above, preferably methoxy) in an appropriate solvent like, for example, N,N-dimethylformamide and in the presence of an acidic catalyst like para-toluenesulphonic acid.

It is appropriate to note that the compounds of the invention in their various forms: acid, salt, ester, amide or lactone, can be interconverted according to the processes described above, and consequently these various forms also constitute intermediates which can be used for the synthesis of the compounds according to the invention.

The mixtures of stereoisomers (cis, trans, threo, erythro, enantiomers) can be separated by the usual methods at the most appropriate of the synthesis.

Usual methods is intended to mean all the processes familiar to the specialist, like, for example, recrystallization, chromatography or the formation of combinations with optically active compounds.

The synthesis intermediate compounds corresponding to the formulae 2, 4, 5, 6, 7, 8, 9, 10, 11 and 14 also form part of the invention, with the exception of the products of formula 5 where $R_1$ and $R_2$ denote H and X denotes S or $CH_2$, some of these compounds being known according to Degani, Ann. Chem. (Rome) 1971, 61(2), p 793 to 813 and according to Penn, J. Magn. Reson. 1975, 18 (1), p 6 to 11.

The present invention also relates to the processes for preparing these synthesis intermediates.

The compounds of formula 1 have the property of inhibiting the 3-hydroxy-3-methylglutaryl coenzyme A reductase and consequently exert a powerful hypocholesterolaemiant effect.

The compounds of formula 1 are also capable of antagonizing the receptors of thromboxane $A_2$, a property which is reflected in an antiaggregating action on platelets.

These properties of the compounds of the invention make them particularly advantageous in use as medication for the treatment of various cardiovascular disorders like, for example, the thrombotic symptoms of diabetes, atherosclerosis and hyperlipoproteinaemias.

Furthermore, the compounds of the invention are endowed with antifungal properties which give them a great advantage as medications with antimycotic action.

The pharmacological properties of the compounds according to the invention have been demonstrated by the following tests.

Test A: Measurement of hepatic $^{14}C$-cholesterogenesis, in vivo, in the rat according to the method described by Bucher et al., J Biol. Chem., 222, 1-15, 1956 and Alberts et al., Proc. Natl. Acad. Sci. USA, 77 (7), 3957-3961, 1980.

Test B: Measurement of total cholesterolaemia, "in vivo", in the rat treated intravenously with triton WR 1339 according to the method described by Endo et al., Biochim. Biophys. Acta, 575, 226-276, 1979.

Test C: Measurement of platelet aggregation induced by an agonist of $TXA_2$ receptors, in the guinea pig in the following manner: platelet-rich plasmas (PRP) are prepared by aortic punction of anaesthetized animals; the blood (9 vol.) is collected onto a 106 mM solution of trisodium citrate (1 vol.) to prevent coagulation. The PRPs are isolated by slow centrifuging (10 min, 380 g), and left to incubate for at least 3 min (37° C., with slow stirring) in an aggregometer of the Chronolog-400 type. The platelet aggregation is induced by addition of a direct agonist of the $TXA_2$ receptors, such as, for example, the compound known by the code name U 46619 (at a concentration of 20 nM) according to Malmstein, Life Sci., 18, 169-178, 1976; the compounds of the invention are tested "in vitro".

For example, in the test A, ED 50 values of 0.17 mg/kg, 0.6 mg/kg, 0.09 mg/kg and 0.38 mg/kg were obtained respectively for compounds No. 1, 2, 19 and 65, and, under the same conditions, an ED 50 of 0.39 mg/kg for Lovastatine.

In the test B, ED 25 values of 29, 100, 110 mg/kg and 74 mg/kg were obtained respectively for the same compounds and, under the same conditions, an ED 25 of 130 mg/kg for Lovastatine.

In the test C, IC 50 values of 91 and $28 \times 10^{-6}$ moles/liter were obtained for compounds No. 1 and 19.

The present invention also relates to the medications consisting of the compounds of general formula 1 taken as such, in the pure state or in the form of combinations with any other product which is acceptable from a pharmaceutical viewpoint, which may be inert or physiologically active.

These medications may be administered according to a wide variety of different posological forms, such as tablets, gelatin capsules, capsules, powders, granulates, and the like. In these compositions, the active principle is mixed with one or more inert diluents such as lactose or starch; in addition, these compositions may include substances other than diluents, for example lubricants such as talc or magnesium stearate; when aqueous suspensions, elixirs or syrups for oral administration are desired, the essential active ingredient may be combined therein with various sweeteners and/or flavours, if appropriate with emulsifiers and/or suspending agents at the same time as diluents such as water, ethanol, propylene glycol and various similar combinations.

The pharmaceutical compositions according to the invention, suitable for oral administration and presented in the form of a single dose, contain from 1 to 500 mg of active principle.

The following example, given without any limitation being implied, illustrates a composition of this type.

EXAMPLE

| Active principle | 10 mg |
|---|---|
| Lactose | 104 mg |
| Wheat starch | 30 mg |
| Talc | 2.5 mg |
| Polyvidone excipient | 3 mg |
| Magnesium stearate | 0.5 mg |

The invention is illustrated by the nonlimiting examples below, in which:

Unless stated otherwise, all the evaporations are performed in a rotary evaporator under reduced pressure.

The temperatures are expressed in degrees centigrade (°C.).

When "room temperature" is indicated, this is a temperature of between 18° and 25° C.

Unless stated otherwise, the degree of progress of the reaction is monitored by thin layer chromatography (TLC).

Where appropriate, new compounds are characterized by their physical constants, melting point shown as MP or boiling point shown as B, if applicable followed by the indication of the pressure, expressed in millibars.

The yields which may be shown are given solely by way of illustration and are not the highest which are possible.

Unless stated otherwise, the nuclear magnetic resonance spectra are those of protons and are recorded at 60 MHz in the presence of tetramethylsilane as internal standard; the chemical shifts are given in ppm; the signals are described using the following abbreviations: s=singlet, d=doublet, dd=pair of doublets, t=triplet, q=quadruplet, m=multiplet.

The infrared spectra of the compounds are recorded using samples dispersed in potassium bromide in the case of solid compounds or as a film in the case of liquids.

EXAMPLE 1

(+,−)Ethyl 6E-erythro-7-(4-(4-fluorophenyl)-3-spiro-(2,1′-cyclopentyl-2H-1-benzopyran))-3,5-dihydroxyhept-6-enoate (compound No. 1—formula 1: X=O, $R_1$-$R_2$=—$(CH_2)_4$—, $R_3$=4′F, $R_4$=$R_5$=$R_6$=$R_9$=$R_{10}$=H, $R_7$-$R_8$=bond, $R_{11}$=$OC_2H_5$).

STAGE 1

4-(4-Fluorophenyl)-3,4-dihydro-4-hydroxyspiro(2H-1-benzopyran-2,1′-cyclopentane)—(Scheme VI—formula 14)

The operation is carried out under nitrogen atmosphere in a reactor protected against moisture. 43.75 g (0.25 moles) of 1-bromo-4-fluorobenzene in solution in 200 cm³ of diethyl ether are added, so as to keep the ether refluxing gently, to 6.07 g (0.25 g-atoms) of magnesium turnings in suspension in 130 cm³ of diethyl ether.

The mixture is kept refluxing for 4 hours and is then cooled to room temperature and, at this temperature, a solution of 20 g (0.1 moles) of spiro(2H-1-benzopyran-2,1′-cyclopentan-4-one) [prepared according to Kabbe et al., Synthesis 12, 886, 1978] in 60 cm³ of diethyl ether is added at the rate needed to keep the ether refluxing gently.

The mixture is stirred for 2 hours at room temperature and is then poured onto an iced aqueous solution of ammonium chloride in a large excess relative to the stoichiometry; a quantity of dilute hydrochloric acid sufficient to dissolve the suspension completely is added and the organic phase is separated off; it is washed with water to neutral pH, is dried over sodium sulphate, filtered and the solvent is evaporated off; 30 g of oil are obtained and used as such in the synthesis which follows.

STAGE 2

4-(4-Fluorophenyl)spiro(2H-1-benzopyran-2,1′-cyclopentane) (Scheme VI—formula 5)

A mixture of 30 g (0.1 moles) of the crude product from stage 1 and of 3 g of $KHSO_4$ (1/10 of the weight of the compound to be treated) is heated for 30 minutes under reduced pressure (16 mm Hg) to a temperature of 120° C. The residue is dissolved in the necessary quantity of dichloromethane, this solution is washed with water and is then dried over sodium sulphate, is filtered and the solvent is evaporated off; the solid obtained is dispersed in methyl alcohol.

MP=76°-8° C. (diisopropyl ether)—Yield=75%.

(TLC: silica gel:ethyl acetate (AcOEt)-hexane: 5-95:1 spot)

| Percentage analysis: $C_{19}H_{17}FO$ MW = 280.33 | | | |
|---|---|---|---|
| | C | H | F |
| % calculated | 81.40 | 6.11 | 6.78 |
| % found | 81.53 | 6.20 | 6.76 |

NMR ($CDCl_3$): 1.25-2.70 (m,8H); 5.73 (s, 1H); 6.50-7.87 (m, 8H).

STAGE 3

2E-3-(4-(4-Fluorophenyl)-3-spiro(2,1′-cyclopentyl-2H-1-benzopyran))prop-2-enal (Scheme II—formula 2)

The operation is carried out under nitrogen atmosphere in a reactor protected against moisture Unless stated otherwise, the temperature of the reaction mixture is kept at −20° C. during the following operations. 29.1 g (0.19 moles) of phosphorus oxychloride are added with stirring over 30 min to a solution of 20.9 g (0.2 moles) of N,N-dimethyl-3-aminoacrolein in 200 cm³ of acetonitrile; stirring is continued for 10 min and 11.2 g (0.04 moles) of the compound from stage 2 in solution in 100 cm³ of acetonitrile are then added over 15 min. The mixture is then allowed to return to room temperature and is then heated under reflux until the disappearance of the starting material, monitored by thin layer chromatography; in the present case, the heating time needed is 40 hours.

The mixture is evaporated down and the residue is then poured into 1000 cm³ of iced water and is neutralized (pH=9) by adding the necessary quantity of concentrated sodium hydroxide, the solution is stirred for 15 min and is then extracted with 1000 cm³ of methylene chloride (2×500 cm³).

The organic layer is washed with water, is dried over sodium sulphate, is filtered, 1000 cm³ of hexane are added to it and it is stirred in the presence of 100 g of silica gel. After filtration and evaporation an oil is obtained, which crystallizes to a yellow solid when dispersed in hexane.

M.P.=108°-11° C. (diisopropyl ether)—Yield=8.4 g=63%

(TLC: silica gel:AcOEt-hexane: 1-9:1 spot)

| Percentage analysis: $C_{22}H_{19}FO_2$ MW = 334.37 | | | |
|---|---|---|---|
| | C | H | F |
| % calculated | 79.02 | 5.73 | 5.68 |
| % found | 78.82 | 5.75 | 5.65 |

IR: γCHO: 1670 cm⁻¹.

N.M.R. ($CDCl_3$): 1.25-2.87 (m, 8H); 5.98 (dd, 1H J=17 Hz and 7 Hz); 6.37-7.5 (m, 9H); 9.25 (d, 1H J=7Hz).

STAGE 4

(+,−)Ethyl 6E-7-(4-(4-fluorophenyl)-3-spiro(2,1′-cyclopentyl-2H-1-benzopyran))-5-hydroxy-3-oxohept-6-enoate (Scheme I—formula 4)

The operation is carried out under nitrogen atmosphere and in the absence of moisture, the temperature of the mixture being kept at −20° C. unless stated otherwise. 5.6 g (0.043 moles) of ethyl acetoacetate in solution in 25 cm³ of THF are added to a suspension of 1.2 g (0.05 moles) of sodium hydride in 300 cm³ of tetrahydrofuran (THF); the mixture is stirred for 20 min and 27 cm³ of a 1.6N solution of butyllithium in hexane (that is 0.043 moles of BuLi) are then added to it over 15-20 min; stirring of the mixture is continued for 20 min and a solution of 8.7 g (0.026 moles) of the aldehyde from stage 3 in 140 cm³ of THF is then added to it dropwise. Stirring of the mixture is continued for 3 hours and 40 ml of a 3N solution of hydrochloric acid are then added to it dropwise at between −20° C. and 10° C. After extraction with ethyl acetate, the organic phase is washed with water to pH 7, is dried over sodium sulphate and is then evaporated to dryness; an oil is obtained, which crystallizes when dispersed in hexane.

M.P.=87°–90° C. (ethyl acetate)—Yield=110 g=90.9%.

(TLC: silica gel:AcOEt-hexane: 1-2:1 spot).

| Percentage analysis: $C_{28}H_{29}FO_5$ MW = 464.51 | | | |
|---|---|---|---|
| | C | H | F |
| % calculated | 72.40 | 6.29 | 4.09 |
| % found | 72.33 | 6.31 | 4.05 |

IR: $\gamma OH$: 3420 cm$^{-1}$; $\gamma CO$: 1740 and 1710 cm$^{-1}$.

N.M.R (CDCl$_3$): 1.32 (t, 3H); 1.5–2.35 (m, 8H); 2.52 (d, 2H); 3.92–4.65 (m, 3H)); 5.30 (dd, 1H J=15.8 Hz and 5.5 Hz); 6.00 (d, 1H J=15.8 Hz); 6.25–7.50 (m, 8H).

STAGE 5

(+,−)Ethyl 6E-erythro-7-(4-(4-fluorophenyl)-3-spiro(2,1'-cyclopentyl-2H-1-benzopyran))-3,5-dihydroxyhept-6-enoate (compound No. 1)

The operation is carried out under nitrogen atmosphere, in a reactor protected against moisture.

Unless stated otherwise, the temperature of the reaction mixture is kept at −70° C. during the following operations. 7.7 cm$^3$ of a 1N solution of diethylmethoxyborane in THF (that is 0.007 moles + 10% of borane) is added with stirring over 5 min to a solution of 3.25 g (0.007 moles) of the keto ester from stage 4, in a mixture of 65 cm$^3$ of THF and of 15 cm$^3$ of methanol.

Stirring of the mixture is continued for 40 min and 0.29 g (0.007 moles + 10%) of sodium borohydride are then added to it. Stirring of the mixture is continued for 5 hours and the latter is then acidified by addition of 6.5 cm$^3$ of acetic acid, after which 80 cm$^3$ of ethyl acetate are added to it.

The temperature of the mixture is allowed to return to room temperature; the mixture is then washed with a saturated aqueous solution of sodium bicarbonate (2×200 cm$^3$) and then with water; the organic phase is separated off, is dried over sodium sulphate and the solvent is then evaporated off. The residual oil obtained is dissolved in 60 cm$^3$ of methanol; this solution is stirred for 20 min at 35° C. and is then evaporated to dryness. This operation is renewed to a constant weight; in the present case the operation is renewed 4 times.

3.1 g of a solid are thus obtained and are dispersed in diisopropyl ether.

M.P.=112°–4° C. (ethyl acetate)—Yield=2.48 g=76%.

(TLC: silica gel:AcOEt-hexane: 1-1:1 spot).

| Percentage analysis: $C_{28}H_{31}FO_5$ MW = 466.55 | | | |
|---|---|---|---|
| | C | H | F |
| % calculated | 72.08 | 6.70 | 4.07 |
| % found | 71.82 | 6.83 | 3.90 |

I.R.: $\gamma OH$: 3390 cm$^{-1}$; $\gamma CO$: 1715 cm$^{-1}$.

N.M.R. (CDCl$_3$)−200 MHz: 1.27 (t, 3H); 1.20–1.58 (m, 2H); 1.60–2.29 (m, 8H); 2.36–2.44 (m, 2H); 4.17 (q, 2H); 4.00–4.29 (m, 2H); 5.34 (dd, 1H J=16.1 Hz and J=6.3 Hz); 5.94 (dd, 1H J=16.1 Hz and 1.2 Hz); 6.54 (dd, 1H J=7.7 Hz and 1.5 Hz); 6.70–6.85 (m, 2H); 7.00–7.20 (m, 5H).

H.P.L.C.: 25 cm spherosyl 5 u silica column; 254 nm UV detection; mobile phase: AcOEt-hexane-AcOH: 35-65-0.01 1 peak: (11.1 min).

EXAMPLE 2

(±)Methyl 6E-erythro-7-(1,2-dihydro-2,2-dimethyl-4-phenyl-3-naphthyl)-3,5-dihydroxyhept-6-enoate (compound No. 2—formula 1: X=CH$_2$; R$_1$=R$_2$=CH$_3$; R$_3$=R$_4$=R$_5$=R$_6$=R$_9$=R$_{10}$=H; R$_7$ and R$_8$=bond; R$_{11}$=OCH$_3$)

STAGE 1

Ethyl 2-(2,2-dimethyl-3-phenylpropyl)cyanoacetate (Scheme VII—formula 15)

A solution of 100 g (0.79 moles) of benzyl chloride in 400 cm$^3$ of ether is added so as to keep a gentle reflux to a suspension of 19.2 g (0.79 gram-atoms) of magnesium turnings in 100 cm$^3$ of ether.

The mixture is heated to reflux for 15 min and a solution of 101.1 g (0.66 moles) of ethyl isopropylidenecyanoacetate in 130 cm$^3$ of ether is then added so as to keep a gentle reflux.

The materials are heated to reflux for 2 hours and then cooled and 400 cm$^3$ of water are added slowly followed by 100 cm$^3$ of 20% H$_2$SO$_4$.

The mixture is stirred for 30 min and the organic phase is then separated off. The aqueous phase is extracted with ether, the combined ether phases are dried over sodium sulphate, are filtered and are distilled.

B$_{0.3}$=115°–121° C.—Yield=147 g=90%.

I.R.: $\gamma C=O$: 1740 cm$^{-1}$; $\gamma CN$: 2250 cm$^{-1}$.

N.M.R.: (CDCl$_3$): 1–1.5 (m, 9H); 2.75 (s, 2H); 3.25 (s, 1H); 4.2 (q, 2H); 6.7–7.6 (m, 5H).

STAGE 2

3,3-Dimethyl-4-phenylbutanoic acid (Scheme VII—formula 16)

A solution of 70 g of potassium hydroxide in 230 cm$^3$ of ethylene glycol is added without cooling to 70 g (0.285 moles) of the compound from stage 1. The mixture is heated to reflux (140° C.) for 3 h 15 min. The volatile solvents are evaporated off at a pressure of 15 mm of mercury and the material is then heated to reflux (197° C.) for 6 hours. The mixture is cooled, 500 cm$^3$ of water are added to it and it is extracted with ether. The aqueous phase is acidified by addition of concentrated hydrochloric acid and is extracted with benzene. The benzene phase is washed with water, is dried over sodium sulphate, is filtered and is evaporated to dryness. 48.7 g of an oil are thus isolated and are employed as such in the following synthesis. Yield=89%.

I.R.: $\gamma C=O$: 1700 cm$^{-1}$.

N.M.R. (CDCl$_3$): 1 (s, 6H); 2.2 (s, 2H); 2.65 (s, 2H); 6.8–7.5 (m, 5H).

STAGE 3

1,2,3,4-Tetrahydro-3,3-dimethyl-1-oxonaphthalene (Scheme VII—formula 12)

A mixture of 292 g of polyphosphoric acid and of 860 cm$^3$ of xylene is heated between 70° and 80° C. and 48.7 g (0.253 moles) of the compound from stage 2 in solution in 550 cm$^3$ of xylene are added at this temperature. The mixture is heated to reflux for 6 h 30 min and is then cooled and the xylene phase is separated off; 2000 cm$^3$ of water are added to the remaining inorganic phase, which is extracted with xylene. The organic phases are combined, are washed with a 10% strength aqueous solution of sodium hydroxide and then with water, and are then dried over sodium sulphate. The mixture is filtered, the solvent is evaporated off and the residual oil is distilled.

$B_{0.2} = 72°-90°$ C.—Yield = 87.5%.

I.R.: $\gamma C=O$: 1680 cm$^{-1}$.

N.M.R. (CDCl$_3$): 0.8-1.2 (m, 6H); 2.5 (s, 2H); 2.8 (s, 2H); 7-7.7 (m, 3H); 8 (dd, 1H).

STAGE 4

1,2,3,4-Tetrahydro-1-hydroxy-3,3-dimethyl-1-phenyl-naphthalene (Scheme VI—formula 14)

A solution of 86.95 g (0.55 moles) of bromobenzene in 150 cm$^3$ of ether is added so as to keep the ether refluxing gently to 8.07 g (1.16 gram-atoms) of lithium in suspension in 200 cm$^3$ of ether. The mixture is heated to reflux for 45 min and is then cooled and 38.6 g (0.19 moles) of compound from stage 3 in solution in 150 cm$^3$ of ether are added to it at between 5° and 10° C. The mixture is stirred for 4 hours at room temperature and 150 cm$^3$ of water are then added to it while the temperature is kept between 5° and 10° C. The mixture is stirred for 15 min and the organic phase is then separated off, is washed with water, is dried over sodium sulphate, is filtered and the solvent is evaporated off. A yellow solid is obtained, which is dispersed in hexane, filtered off and dried.

M.P. = 107°-110° C.—Yield = 47.4 g = 85%.

STAGE 5

1,2-Dihydro-2,2-dimethyl-4-phenylnaphthalene (Scheme VI—formula 5) prepared from the compound from stage 4 according to the procedure of stage 2 of Example 1.

$B_{0.1} = 103°-105°$ C.; M.P. = 82°-84° C.; Yield = 89%.

| Percentage analysis: C$_{18}$H$_{18}$ M.W. = 234.34 | | |
|---|---|---|
| | C | H |
| % calculated | 92.26 | 7.74 |
| % found | 92.42 | 7.64 |

N.M.R. (CDCl$_3$): 1.05 (s, 6H); 2.7 (s, 2H); 5.7 (s, 1H); 6.75-7.4 (m, 9H).

STAGE 6

3-Bromo-1,2-dihydro-2,2-dimethyl-4-phenylnaphthalene (Scheme III—formula 6)

25 g (0.14 moles) of N-bromosuccinimide in solution in 120 cm$^3$ of DMF are added to a suitably stirred suspension of 27.3 g (0.117 moles) of the compound from stage 5 in 120 cm$^3$ of DMF, at such a rate that the temperature of the mixture does not exceed 30° C. Stirring of the mixture is continued at room temperature for 24 hours and it is then allowed to stand for 48 hours; the mixture is then poured onto 800 cm$^3$ of iced water, is extracted with 400 cm$^3$ of ether (2 × 200 cm$^3$), the combined extracts are washed with water and are then dried over sodium sulphate; the ether is evaporated off and the residual oil is chromatographed on silica gel, using hexane as eluent. After evaporation of the hexane an oil is obtained, which is employed as such in the synthesis which follows.

Yield = 32.4 g = 89%.

N.M.R. (CDCl$_3$): 1.2 (s, 6H); 2.95 (s, 2H); 6.3-7.5 (m, 9H).

STAGE 7

3E-3-(1,2-Dihydro-2,2-dimethyl-4-phenyl-3-naphthyl)-prop-2-enal (Scheme III—formula 2)

Unless stated otherwise, the operations which follow are carried out at a temperature of −50° C. 13.8 cm$^3$ of a 1.6N solution of butyllithium in hexane (that is 0.022 moles of BuLi) are added to a solution of 6.26 g (0.02 moles) of the compound from stage 6 in 100 cm$^3$ of ether cooled to −50° and suitably stirred. The temperature of the mixture is then allowed to return to room temperature, the mixture is heated to reflux for 1 h 20 min and is then cooled to between −50° and −60° C. and 2 of N,N-dimethyl-3-aminoacrolein in solution in 30 cm$^3$ of ether are added to it. Stirring of the mixture is continued at −50° for 1 h 30 min and its temperature is then allowed to return to room temperature; the stirring is continued for 30 min and the whole is then poured onto 300 cm$^3$ of 10% hydrochloric acid with stirring. The organic phase is separated off and is then washed with water; the aqueous phase is extracted with methylene chloride, the extract is washed with water, all the organic phases are combined; they are dried over sodium sulphate; the solvents are evaporated off and the residual oil is crystallized from pentane.

M.P. = 105°-108° C.—Yield = 2.6 g = 45%.

I.R.: $\gamma C=O$: 1680 cm$^{-1}$.

N.M.R. (CDCl$_3$): 1.2 (s, 6H); 2.8 (s, 2H); 6.05 (dd: J = 16.5 and 7.5, 1H); 6.4-7.5 (m, 10H); 9.5 (d: J = 7.5, 1H).

STAGE 8

(±)Methyl 6E-7-(1,2-dihydro-2,2-dimethyl-4-phenyl-3-naphthyl)-5-hydroxy-3-oxohept-6-enoate (Scheme I—formula 4)

Prepared from the compound from stage 7 according to the procedure of stage 4 of Example 1.

The compound is in the form of oil. Yield = 87%.

N.M.R. (CDCl$_3$): 1.1 (s, 6H); 1.9-2.6 (m, 3H); 2.72 (s, 2H); 3.3 (s, 2H); 3.65 (s, 3H); 3.45-4.5 (m, 2H); 4.8-5.35 (m, 1H); 6 (d: J = 15.75, 1H); 6.35-7.5 (m, 5H).

STAGE 9

(+,−)Methyl 6E-erythro-7-(1,2-dihydro-2,2-dimethyl-4-phenyl-3-naphthyl)-3,5-dihydroxyhept-6-enoate (compound No. 2)

Prepared from the compound from stage 8 according to the procedure of stage 5 of Example 1.

Yellow-coloured solid.

M.P. = 101°-103° C.—Yield = 2.2 g = 67%.

| Percentage analysis: C$_{26}$H$_{30}$O$_4$ MW = 406.52 | | |
|---|---|---|
| | C | N |
| % calculated | 76.82 | 7.44 |
| % found | 76.57 | 7.43 |

EXAMPLE 3

(±)Methyl 6E-erythro-7-(4-(4-chlorophenyl)-2,2-dimethyl-2H-benzothiapyran-3-yl)-3,5-dihydroxyhept-6-enoate (compound No. 3—formula 1: X=S, R$_1$, R$_2$=CH$_3$, R$_3$=4'Cl, R$_4$=R$_5$=R$_6$=R$_9$=R$_{10}$=H, R$_7$ and R$_8$=bond, R$_{11}$=OCH$_3$).

STAGE 1

4-(4-Chlorophenyl)-3,4-dihydro-4-hydroxy-2,2-dimethyl-2H-benzothiapyran—(Scheme VI—formula 14) prepared from 2,3-dihydro-2,2-dimethyl-4H-benzothiapyran-4-one according to the procedure of stage 4 of Example 2; employed crude in the synthesis which follows.

STAGE 2

4-(4-Chlorophenyl)-2,2-dimethyl-2H-benzothiapyran—(scheme VI—formula 5) prepared from the compound from stage 1 according to the procedure of stage 2 of Example 1).

M.P. = 100°–102° C. (diisopropyl ether)—Yield = 50%.

| Percentage analysis: $C_{17}H_{15}ClS$ MW 286.81 | | | | |
| --- | --- | --- | --- | --- |
| | C | H | Cl | S |
| % calculated | 71.19 | 5.27 | 12.36 | 11.18 |
| % found | 70.94 | 5.42 | 12.60 | 10.90 |

N.M.R. (CDCl$_3$): 2 (s, 6H); 5.75 (s, 1H); 6.75–7.5 (m, 8H).

STAGE 3

3-Bromo-4-(4-chlorophenyl)-2,2-dimethyl-2H-benzothiapyran—(Scheme III—formula 6) prepared from the compound from stage 2 according to the procedure of stage 6 of Example 2; after evaporation of the ether, a solid is obtained, which is dispersed in the necessary quantity of methanol cooled to −20° C. and the solid formed is then filtered off and dried.

M.P. = 150°–156° C.—Yield = 88%.
N.M.R. (CDCl$_3$): 1.6 (s, 6H); 6.2–7.8 (m, 8H).

STAGE 4

Ethyl 2E-3-(4-(4-chlorophenyl)-2,2-dimethyl-2H-benzothiapyran-3-yl)prop-2-enoate (scheme IV—formula 8)

The operation is carried out under nitrogen atmosphere in a reactor protected against atmospheric moisture. A mixture of 20.1 g (0.055 moles) of the compound from stage 3, 27.5 cm$^3$ (0.254 moles) of ethyl acrylate, 130 cm$^3$ of N,N-dimethylformamide, 130 cm$^3$ of triethylamine, 1 g of tri-ortho-tolyl-phosphine and 0.25 g of palladium diacetate is heated to reflux for 4 hours; the mixture is poured onto a mixture of ice and water and is extracted with the necessary quantity of ether; this ether extract is washed alternately with hydrochloric acid and with water to pH=7 and is then dried over sodium sulphate, filtered, the ether is evaporated off, the residue is dispersed under hexane cooled to −20° C. and the solid formed is then filtered off and dried.

M.P. = 97°–99° C. (CH$_3$OH)—Yield = 91%

| Percentage analysis: $C_{22}H_{21}ClO_2S$ MW = 384.91 | | | | |
| --- | --- | --- | --- | --- |
| | C | H | Cl | S |
| % calculated | 68.65 | 5.50 | 9.21 | 8.33 |
| % found | 68.58 | 5.79 | 9.45 | 8.30 |

N.M.R. (CDCl$_3$): 1–1.75 (m, 9H); 3.75–4.5 (9, 2H); 5.3–5.75 (d, 1H); 6.5–7.5 (m, 9H).

STAGE 5

2E-3-(4-(4-Chlorophenyl)-2,2-dimethyl-2H-benzothiapyran-3-yl)prop-2-enol (scheme IV—formula 9)

The operation is carried out under nitrogen atmosphere in a reactor protected against atmospheric moisture. 196 cm$^3$ of a 1N solution of diisobutylaluminium hydride in tetrahydrofuran (that is: 0.049 × 4 moles of DIBAL) are added to a solution of 18.9 g (0.049 moles) of compound from stage 4 in 180 cm$^3$ of tetrahydrofuran cooled to −20° C.; the mixture is stirred at room temperature for 1 hour and 200 cm$^3$ of water are then added to the mixture; this addition is exothermic, the rate is controlled so as to keep the temperature of the mixture below 30° C.; the mixture is then acidified to pH=1 by addition of the necessary quantity of concentrated hydrochloric acid and is then extracted with ether. The ether phase is then washed with water to neutrality and is then dried over sodium sulphate; after filtration followed by evaporation of the ether, an oil is obtained which is dispersed in the necessary quantity of hexane cooled to 5° C.; the solid formed is filtered off and dried.

M.P. = 105°–108° C. (hexane)—Yield = 87%.

| Percentage analysis: $C_{20}H_{19}ClOS$ MW = 342.87 | | | | |
| --- | --- | --- | --- | --- |
| | C | H | Cl | S |
| % calculated | 70.06 | 5.59 | 10.34 | 9.35 |
| % found | 69.91 | 5.78 | 10.52 | 9.30 |

STAGE 6

2E-3-(4-(4-Chlorophenyl)-2,2-dimethyl-2H-benzothiapyran-3-yl)prop-2-enal (scheme IV—formula 2)

The operation is carried out in a reactor protected against atmospheric moisture; a mixture of 14.63 g (0.0427 moles) of compound from stage 5, of 22.26 g (0.0427 × 6 moles) of manganese dioxide and 300 cm$^3$ of dichloromethane is stirred at room temperature for 48 h; the mixture is then filtered, the dichloromethane is evaporated from the filtrate, the solid residue is dispersed in the necessary quantity of diisopropyl ether, is filtered off and is dried.

M.P. = 132°–134° C. (CH$_3$CO$_2$C$_2$H$_5$)—Yield = 82%.

| Percentage analysis: $C_2H_{17}ClOS$ MW = 340.86 | | | | |
| --- | --- | --- | --- | --- |
| | C | H | Cl | S |
| % calculated | 70.47 | 5.03 | 10.40 | 9.41 |
| % found | 70.27 | 4.98 | 10.51 | 9.85 |

N.M.R. (CDCl$_3$): 1.5 (s, 6H); 5.75–6.25 (9, 1H); 6.75–7.5 (m, 9H); 9.25–9.5 (d, 1H).

STAGE 7

(+,−)Methyl 6E-7-(4-(4-chlorophenyl)-2,2-dimethyl-2H-benzothiapyran-3-yl)-5-hydroxy-3-oxohept-6-enoate (scheme I—formula 4)

Prepared from the compound from stage 6 according to the procedure of stage 4 of Example 1.
M.P. = 86°–88° C. (CH$_3$OH)—Yield = 94%.
I.R.: γC=O: 1740 and 1700 cm$^{-1}$.

N.M.R (CDCl$_3$): 1.5 (s, 6H); 2.25-2.75 (m, 3H); 3.3 (s, 2H); 3.75 (s, 3H); 4.25-4.5 (m, 1H); 5-5.55 (dd, 1H); 5.75-6.25 (d, 1H); 6.5-7.5 (m, 8H).

STAGE 8

(±)Methyl 6E-erythro-7-(4-(4-chlorophenyl)-2,2-dimethyl-2H-benzothiapyran-3-yl)-3,5-dihydroxyhept-6-enoate (scheme I—formula 1).

Prepared from the compound from stage 7 according to the procedure of stage 5 of Example 1.
M.P.=115°-117° C. (diisopropyl ether)—Yield=58%.

| Percentage analysis: C$_{25}$H$_{27}$ClO$_4$S MW = 458.99 | | | |
|---|---|---|---|
| | C | H | Cl | S |
| % calculated | 65.42 | 5.93 | 7.72 | 6.98 |
| % found | 65.52 | 6.02 | 7.80 | 7.09 |

I.R.: $\gamma CO = 1720$ cm$^{-1}$; $\gamma OH = 3400$ cm$^{-1}$.
N.M.R. (CDCl$_3$): 1.5 (s, 6H); 2.5 (d, 2H); 3-3.75 (m, 2H); 3.75 (s, 3H); 4-4.5 (m, 2H); 5-5.5 (dd, 1H); 5.75-6.25 (d, 1H); 6.5-7.5 (m, 8H).

EXAMPLE 4

(+,−)Ethyl erythro-7-(4-(4-fluorophenyl)-3-spiro(2,1'-cyclopentyl-2H-1-benzopyran))-3,5-dihydroxyheptanoate (compound 4—formula 1: X=O, R$_1$-R$_2$=(CH$_2$)$_4$—, R$_3$=4'F, R$_4$=R$_5$=R$_6$=R$_7$=R$_8$=R$_9$=R$_{10}$=H, R$_{11}$=OC$_2$H$_5$).

STAGE 1

3E-3-(4-(4-Fluorophenyl)-3-spiro(2,1'-cyclopentyl-2H-1-benzopyran))prop-2-enal dimethylacetal (Scheme V—formula 10)

The operation is carried out under nitrogen atmosphere in a reactor protected against moisture. A mixture of 16.75 g (0.05 moles) of 3E-3-(4-(4-fluorophenyl)-3-spiro(2,1'-cyclopentyl-2H-1-benzopyran))prop-2-enal, itself prepared from spiro(2H-1-benzopyran-2,1'-cyclopentan-4-one) according to the procedures of stages 1, 2 and 3 of Example 1, and of 2.25 g of Amberlyst 15 resin is stirred for 7 hours at room temperature in 625 cm$^3$ of methyl orthoformate. 2.25 g of Amberlyst resin are added again and the mixture is stirred at room temperature for 12 hours. This treatment is repeated 4 times in succession and the material is then filtered, and the excess methyl orthoformate is evaporated off; a white solid is isolated and is dispered under hexane; it is filtered off and dried.
M.P.=112°-114° C.—Yield=16.3 g=88%.
N.M.R. (CDCl$_3$): 2.1-2.2 (m-8H); 3.07 (s, 6H); 6.05 (d, 1H, J=5 Hz); 5.3 (dd, 1H, J=5 Hz and 16 Hz); 6.05 (d, 1H, J=16 Hz); 6.3-7.2 (m, 8H).

STAGE 2

3-(4-(4-Fluorophenyl)-3-spiro(2,1'-cyclopentyl-2H-1-benzopyran))propanal dimethylacetal (Scheme V—formula 11)

3.8 g (0.01 moles) of the compound from stage 1 in solution in 100 cm$^3$ of THF are hydrogenated at normal pressure and at room temperature in the presence of 0.5 g of palladium dispersed on carbon. When the theoretical volume of hydrogen to be absorbed is reached, the mixture is filtered and the THF is evaporated off; an oil is obtained, which crystallizes on standing; the solid thus obtained is dispersed in hexane and is then filtered off and dried.
M.P.=83°-85° C.—Yield=3.2 g=84%.
(TLC: silica gel:AcOEt-hexane: 1-9:1 spot).
N.M.R. (CDCl$_3$): 1.9-2.5 (m, 12H); 3.2 (s, 6H); 4.15 (t, 1H, J=5 Hz); 6.3-7.25 (m, 8H).

STAGE 3

3-(4-(4-Fluorophenyl)-3-spiro(2,1'-cyclopentyl-2H-1-benzopyran))propanal (Scheme V—formula 2)

A mixture of 2 g (0.0052 moles) of compound from stage 2 and 2 g of Amberlyst 15 resin is stirred at room temperature for 96 hours; the resin is filtered off, the filtrate is evaporated to dryness, the residue is taken up with 40 cm$^3$ of methylene chloride, is washed with water and is dried over sodium sulphate, is filtered and is evaporated to dryness; 0.9 g of oil are thus obtained.
M.P.=118°-120° C. (diisopropyl ether).
I.R.: $\gamma C=O$: 1720 cm$^{-1}$.
N.M.R. (CDCl$_3$): 1-2.5 (m, 10H); 6.2-7.2 (m, 8H); 9.55 (s, 1H)

| Percentage analysis: C$_{22}$H$_{21}$FO$_2$ MW = 336.39 | | |
|---|---|---|
| | C | H | F |
| % calculated | 78.55 | 6.29 | 5.65 |
| % found | 78.33 | 6.04 | 5.57 |

STAGE 4

(±) Ethyl 7-(4-(4-fluorophenyl)-3-spiro(2,1'-cyclopentyl-2H-1-benzopyran))-5-hydroxy-3-oxo-heptanoate (Scheme I—Formula 4—R$_7$=R$_8$=H)

Prepared from the compound from stage 3 and according to the procedure of stage 4 of Example 1. The compound is obtained in the form of oil (yield=51%); it is employed as such in the synthesis which follows.

STAGE 5

(+,−)Ethyl erythro-7-(4-(4-fluorophenyl)-3-spiro(2,1'-cyclopentyl-2H-1-benzopyran))-3,5-dihydroxyheptanoate (compound No. 4)

Prepared by reduction of the compound from stage 4 according to the procedure of stage 5 of Example 1. White compound.
M.P.=103°-105° C. (diisopropyl ether)—Yield=65%.

| Percentage analysis: C$_{28}$H$_{33}$FO$_5$ MW = 468.54 | | |
|---|---|---|
| | C | H | F |
| % calculated | 71.77 | 7.10 | 4.05 |
| % found | 71.63 | 7.11 | 3.98 |

N.M.R. (CDCl$_3$): 0.9-2.25 (m, 17H); 2.35 (d, 2H, J=6 Hz); 3-3.5 (m, 2H); 3.5-3.9 (m, 1H); 3.9-4.4 (m, 3H); 6.2-7.2 (m, 8H).

EXAMPLE 5

(+,−)Sodium 6E-erythro-7-(4-(4-fluorophenyl)-3-spiro(2,1′-cyclopentyl-2H-1-benzopyran))-3,5-dihydroxyhept- 6-enoate (compound No. 5—formula 1: X=O, $R_1$-$R_2$=—$(CH_2)_4$—; $R_3$=4′F; $R_4$=$R_5$=$R_6$=$R_9$=$R_{10}$=H; $R_7$ and $R_8$=bond; $R_{11}$=—O$^-$Na$^+$)

2.14 g. (0.0046 moles) of compound No. 4 in 30 cm$^3$ of ethanol are heated to 60° C. so as to obtain a clear solution, and this solution is then cooled to room temperature and an aqueous solution of sodium hydroxide, prepared beforehand by dissolving 0.18 g (0.0046 moles) of sodium hydroxide pellets in 100 cm$^3$ of water, is added to it. The mixture is stirred for 30 min, is filtered and is evaporated to dryness; the residue is dried by heating to 60° C. at reduced pressure (0.5 mm Hg) for 1 hour.

M.P.=undefined—Yield=2.04 g=96%.

(TLC: silica gel:AcOEt-hexane: 1-1+3% AcOH:1 spot).

| Percentage analysis: $C_{26}H_{26}FNaO_5$ - MW 460.47 | | | | |
|---|---|---|---|---|
| | C | H | F | Na |
| % calculated | 67.82 | 5.69 | 4.13 | 4.99 |
| % found | 67.44 | 5.71 | 3.91 | 5.11 |

EXAMPLE 6

(+,−)Benzyl 6E-erythro-7-(4-(4-fluorophenyl)-3-spiro(2,1′-cyclopentyl-2H-1-benzopyran))-3,5-dihydroxyhept-6-enoate (compound No. 6—formula 1: X=O, $R_1$-$R_2$=—$(CH_2)_4$—, $R_3$=4′F, $R_4$=$R_5$=$R_6$=$R_9$=$R_{10}$=H, $R_7$ and $R_8$=bond, $R_{11}$=$C_6H_5CH_2O$—)

0.638 g (0.00337 moles+10%) of benzyl bromide are added to a solution of 1.55 g (0.00337 moles) of compound No. 5 in 40 cm$^3$ of methyl ethyl ketone and the mixture is then heated to reflux for 3 hours. 0.638 g of benzyl bromide are added again and the mixture is heated to reflux for 8 hours. The mixture is filtered, the filtrate is evaporated off, the residue is dissolved in the necessary quantity of ethyl acetate, this solution is washed with water, is dried over sodium sulphate, is filtered and is evaporated to dryness. The residual oil is chromatographed on 15 g of silica gel, using an ethyl acetate-hexane mixture: 30–70%. Fraction II collected yields, after evaporation of the solvents, a solid which is dispersed in diisopropyl ether. The solid is filtered off and dried M.P.=81°-83° C.—Yield=1.17 g=66%.

| Percentage analysis: $C_{33}H_{33}FO_5$ MW = 528.59 | | | |
|---|---|---|---|
| | C | H | F |
| % calculated | 74.98 | 6.29 | 3.59 |
| % found | 74.91 | 6.23 | 3.55 |

N.M.R. (CDCl$_3$): 1.1-2.3 (m,,10H); 2.45 (d, 2H J=6.7 Hz); 2.7-3.2 (m, 1H (D$_2$O)); 3.3-3.6 (m, 1H (D$_2$O)); 3.8-4.5 (m, 2H); 5.0-5.6 (s+d, 3H); 5.9 (d, 1H J=15.7 Hz); 6.3-7.7 (m, 13H).

EXAMPLE 7

(+,−)-6E-erythro-7-(4-(4-Fluorophenyl-3-spiro-(2,1′-cyclopentyl-2H-1-benzopyran))-3,5-dihydroxy-N-methylhept-6-enamide (compound No. 7—formula 1: X=O, $R_1$-$R_2$=—$(CH_2)_4$—, $R_3$=4′F, $R_4$=$R_5$=$R_6$=$R_9$=$R_{10}$=H, $R_7$ and $R_8$=bond, $R_{11}$=CH$_3$NH—)

A solution of 0.67 g (0.00165 moles) of compound No. 1 in 25 cm$^3$ of a 33% strength solution of methylamine in ethanol is stirred for 24 hours at room temperature. The solvent is evaporated off and the residue is dispersed in 8 cm$^3$ of ethyl acetate, is filtered and is dried.

M.P.=150°-152° C.—Yield=0.52 g=70%.

| Percentage analysis: $C_{27}H_{30}FNO_4$ MW = 451.54 | | | |
|---|---|---|---|
| | C | H | N | F |
| % calculated | 71.66 | 6.90 | 3.10 | 4.20 |
| % found | 71.47 | 6.76 | 2.93 | 4.08 |

EXAMPLE 8

(+,−)-trans-6-(1E-2-(4-(4-Fluorophenyl)-3-spiro-(2,1′-cyclopentyl-2H-1-benzopyran))ethenyl)-4-hydroxy-3,4,5,6-tetrahydro-2H-pyran-2-one (compound No. 8—formula 1: X=O, $R_1$-$R_2$=—$(CH_2)_4$—, $R_3$=4′F, $R_4$=$R_5$=$R_6$=$R_{10}$=H, $R_7$ and $R_8$=bond, $R_9$ and $R_{11}$=bond)

The operation is carried out in the absence of moisture. A mixture of 6 g (0.0135 moles) of compound No. 4 and of 1.94 g (0.0135 moles) of 2-chloroethyldiethylamine in 120 cm$^3$ of acetone is heated to reflux for 3 hours. The acetone is evaporated off and the residue is dissolved in the necessary quantity of ethyl acetate. The solution is washed with water to pH 7 and is then dried over sodium sulphate. It is filtered and the ethyl acetate is evaporated off. A solid is obtained, which is recrystallized directly from 120 cm$^3$ of ethyl acetate.

M.P.=188°-191° C.—Yield=4.27 g=79%.

| Percentage analysis: $C_{26}H_{25}FO_4$ MW = 420.49 | | | |
|---|---|---|---|
| | C | H | F |
| % calculated | 74.27 | 5.99 | 4.52 |
| % found | 74.07 | 6.04 | 4.49 |

N.M.R. (DMSO-d$_6$)—200 MHz:
1.45-2.20 (m, 10H); 2.34 (dd, 1H J=16 Hz and 3.45 Hz); 3.93-4.10 (m, 1H); 4.85-5.0 (m, 1H); 5.11 (d, 1H J=3.3 Hz); 4.42 (dd, 1H J=16.3 Hz and 6.7 Hz); 6.02 (d, 1H J=16.3 Hz); 6.42-6.54 (m, 1H); 6.72-6.83 (m, 2H); 7.07-7.34 (m, 5H).

EXAMPLE 9

(+,−)-trans-4-Hydroxy-3,4,5,6-tetrahydro-6-(2-(4-(4-fluorophenyl)-3-spiro(2,1′-cyclopentyl-2H-1-benzopyran))ethyl)pyran-2-one (compound No. 9—formula 1: X=O, $R_1$-$R_2$=—$(CH_2)_4$—, $R_3$=4′F, $R_4$=$R_5$=$R_6$=$R_7$=$R_8$=$R_{10}$=H, $R_9$ and $R_{11}$=bond)

1.72 g (0.00409 moles) of compound No. 8 in 70 cm$^3$ of THF are hydrogenated at normal pressure and at room temperature in the presence of 0.1 g of palladium dispersed on carbon. When the theoretical volume of hydrogen to be absorbed is reached, the mixture is filtered, and the filtrate is evaporated and the residue obtained is dispersed in diisopropyl ether The solid thus obtained is filtered off and is dried.

M.P. = 156°–157° C. (diisopropyl ether)—Yield = 0.7 g = 41%.

| Percentage analysis: $C_{26}H_{27}FO_4$ MW = 422.50 | | | |
|---|---|---|---|
| | C | H | F |
| % calculated | 73.91 | 6.44 | 4.50 |
| % found | 73.83 | 6.32 | 4.40 |

N.M.R. (DMSO-$d_6$)—200 MHz: 1.38–2.21 (m, 14H); 2.39 (dd, 1H H = 17.2 Hz and 2.8 Hz); 2.57 (dd, 1H J = 17.2 Hz and 4.6 Hz); 3.96–4.11 (m, 1H); 4.25–4.46 (m, 1H); 5.04 (d, 1H J = 3.2 Hz); 6.31–6.41 (m, 1H); 6.69–6.85 (m, 2H); 7.02–7.34 (m, 5H).

EXAMPLE 10

(+,−)Sodium erythro-7-(4-(4-fluorophenyl)-3-spiro(2,1'-cyclopentyl-2H-1-benzopyran))-3,5-dihydroxyheptanoate (compound No. 10—formula 1: X=O, $R_1$-$R_2$=—$(CH_2)_4$—, $R_3$=4'F, $R_4$=$R_5$=$R_6$=$R_7$=$R_8$=$R_9$=$R_{10}$=H, $R_{11}$=—O$^-$Na$^+$)

A mixture of 0.22 g (0.00052 moles) of compound No. 9 and of 0.52 cm$^3$ (0.00052 moles—5%) of 1N aqueous sodium hydroxide in 25 cm$^3$ of ethanol is stirred at room temperature. The ethanol is evaporated off, the residue is dispersed in ether, and the solid thus obtained is filtered off and dried.

(TLC: silica gel:AcOEt-hexane: 1-1+3% AcOH:1 spot)

M.P. = not defined—Yield = 0.12 g = 50%.

| Percentage analysis: $C_{26}H_{28}FNaO_5$ MW = 462.48 | | | | |
|---|---|---|---|---|
| | C | H | F | Na |
| % calculated | 67.52 | 6.10 | 4.11 | 4.97 |
| % found | 67.30 | 5.92 | 3.90 | 5.00 |

EXAMPLE 11

(+,−)Ethyl erythro-7-(4-(4-fluorophenyl)-3-spiro(2,1'-cyclopentyl-2H-1-benzopyran))-3,5-dihydroxyheptanoate (compound No. 4)

1.4 g (0.003 moles) of compound No. 1 in solution in 100 cm$^3$ of THF are hydrogenated at normal pressure and in the presence of 0.6 g of palladium dispersed on carbon. When the theoretical volume of hydrogen to be absorbed is reached, the mixture is filtered, the filtrate is evaporated to dryness and the residue is dispersed in hexane, is filtered off and is dried.

M.P. = 103°–105° C. (diisopropyl ether)—Yield = 1 g = 71%.

EXAMPLE 12

(+,−)Ethyl trans-(6-(1E-2-(4-(4-fluorophenyl)-3-spiro(2,1'-cyclopentyl-2H-1-benzopyran))ethenyl)-2,2-dimethyl-1,3-dioxan-4-yl)acetate (compound No. 11— formula 1: X=O, $R_1$-$R_2$=—$(CH_2)_4$—, $R_3$=4'F, $R_4$=$R_5$=$R_6$=H, $R_7$ and $R_8$=bond, $R_9$-$R_{10}$=$(CH_3)_2$C—, $R_{11}$=OC$_2$H$_5$)

A mixture of 2 g (0.0043 moles) of compound No. 1, of 0.7 g of 2-methoxypropene and of 8 mg of para-toluenesulphonic acid monohydrate in 25ccm$^3$ of DMF is stirred at room temperature for 48 hours. 125 cm$^3$ of ether are added and the material is washed with a saturated aqueous solution of sodium bicarbonate and then with water. The organic phase is dried over sodium sulphate, is filtered and evaporated to dryness. An oil is obtained and crystallized from hexane. The solid is filtered off, dried and chromatographed on 20 g of silica gel, using a hexane-ethyl acetate: 1-1 mixture as solvent and eluent Combined fractions I and II are evaporated; the residue obtained is crystallized from hexane; the solid is filtered off and dried.

M.P. = 103°–105° C.—Yield = 0.95 g = 44%.

| Percentage analysis: $C_{31}H_{35}FO_5$ MW = 506.61 | | | |
|---|---|---|---|
| | C | H | F |
| % calculated | 73.50 | 6.96 | 3.75 |
| % found | 73.64 | 6.98 | 3.73 |

N.M.R. (CDCl$_3$): 0.9–2.5 (m, 16H); 3.9–4.5 (m, 2H); 4.05 (q, 2H); 5.15 (dd, 1H); 5.95 (d, 1H); 6.2–7.25 (m, 8H).

In the examples of compounds of the invention which follow, the abbreviations employed have the following meanings: Me=methyl, Et=ethyl, Pr=propyl, Bz=benzyl, Pe=n-pentyl, tBu=tert-butyl, iPr=isopropyl, Phe=phenyl, Pyr=pyrrolidino.

EXAMPLE 13

Using the appropriate procedures of Examples 1 to 12, the compounds of formula 1, in which X=O, $R_1$ and $R_2$ form a —$(CH_2)_n$— chain, $R_7$ and $R_8$ together form a single bond, and each of $R_9$ and $R_{10}$ denotes a hydrogen atom, were prepared (table below):

| Compound No. | R3 | R4 | R5 | R6 | n | R11 | M.P. (°C.) |
|---|---|---|---|---|---|---|---|
| 12 | H | H | H | H | 4 | EtO | 119–121 |
| 13 | 4'-Et | H | H | H | 4 | EtO | liquid |
| 14 | H | H | 6-Me | H | 4 | EtO | 96–98 |
| 15 | H | H | 7-F | H | 4 | MeO | 89–96 |
| 16 | 4'-Me | H | H | H | 4 | EtO | 120–122 |
| 17 | 3'-F | H | H | H | 4 | EtO | 97–99 |
| 18 | 4'-MeO | H | H | H | 4 | EtO | 86–88 |
| 19 | 4'-Cl | H | H | H | 4 | EtO | 128–130 |
| 20 | 2',3'-CH=CH—CH=CH | H | H | H | 4 | EtO | 115–117 |
| 21 | 3'-Me | 5'-Me | H | H | 4 | EtO | liquid |
| 22 | 4'-F | H | 5-Me | 7-Me | 4 | MeO | 111–115 |
| 23 | 4'-EtO | H | H | H | 4 | MeO | liquid |
| 24 | 4'-iPrO | H | H | H | 4 | MeO | 78–80 |
| 25 | 4'-F | H | 6-MeO | H | 4 | MeO | liquid |
| 26 | 4'-CF3 | H | H | H | 4 | MeO | 141–143 |

-continued

| Compound No. | R3 | R4 | R5 | R6 | n | R11 | M.P. (°C.) |
|---|---|---|---|---|---|---|---|
| 27 | 4'-PeO | H | H | H | 4 | MeO | 69-71 |
| 28 | 4'-F | H | 7,8-CH=CH—CH=CH | | 4 | MeO | 109-111 |
| 29 | 4'MeS | H | H | H | 4 | MeO | 69-71 |
| 30 | 4'-tBu | H | H | H | 4 | EtO | liquid |
| 31 | 4'-F | H | H | H | 5 | EtO | 128-131 |
| 32 | 4'-F | H | 7-iPrO | H | 4 | MeO | 90-91 |
| 33 | 4'-F | H | H | H | 4 | NH2 | 166-168 |
| 34 | 4'-F | H | H | H | 4 | iPrNH | 118-120 |
| 35 | 4'-Phe | H | H | H | 4 | Pyr | 115-117 |
| 36 | 4'-F | H | H | H | 4 | c-C6H11NH | 104-106 |
| 37 | 4'-F | H | H | H | 4 | BzNH | 90-91 |
| 38 | 4'-Et | H | H | H | 4 | O-Na+ | not defined |
| 39 | H | H | 6-Me | H | 4 | O-Na+ | not defined |
| 40 | 4'-iPr | H | H | H | 4 | O-Na+ | not defined |
| 41 | H | H | H | H | 4 | O-Na+ | not defined |
| 42 | 4'-Cl | H | H | H | 4 | O-Na+ | not defined |

EXAMPLE 14

Using the appropriate procedures of Examples 1 to 12, the compounds of formula 1 in which X=O, $R_4=R_5=R_6=R_9=R_{10}=H$ and $R_7$ and $R_8$ form a bond, were prepared (table below):

| Compound No. | R1 | R2 | R3 | R11 | M.P. (°C.) |
|---|---|---|---|---|---|
| 43 | H | H | H | EtO | 124-125 |
| 44 | Me | Me | 4'-F | MeO | 97-100 |
| 45 | H | iPr | 4'-F | EtO | liquid |

| Compound No. | X | R1 | R2 | R3 | R5 | M.P. (°C.) |
|---|---|---|---|---|---|---|
| 46 | O | —(CH2)4— | | H | H | 180-181 |
| 47 | O | —(CH2)4— | | 4'-F | 6-MeO | 152-154 |
| 48 | CH2 | Me | Me | H | H | 156-158 |
| 49 | S | Me | Me | H | H | 135-137 |

EXAMPLE 16

Using the appropriate procedures of Examples 1 to 12, the compounds of formula 1 in which X=CH2 or S, $R_4=R_6=R_9=R_{10}=H$, $R_7$ and $R_8$ form a single bond, were prepared (table below):

| Compound No. | X | R1 | R2 | R3 | R5 | R11 | MP (°C.) |
|---|---|---|---|---|---|---|---|
| 50 | CH2 | —(CH2)4— | | H | H | MeO | 110-112 |
| 51 | CH2 | Me | Me | 4'-F | H | MeO | 126-128 |
| 52 | CH2 | Me | Me | H | H | MeO | 101-103 |
| 53 | CH2 | —(CH2)4— | | 4'-F | H | MeO | 104-106 |
| 54 | CH2 | —(CH2)4— | | 4'-Cl | H | MeO | 96-98 |
| 55 | CH2 | Me | Me | 4'-Cl | H | MeO | 105-106 |
| 56 | CH2 | —(CH2)4— | | 3'-F | H | MeO | liquid |
| 57 | CH2 | H | H | 4'-F | H | O-Na+ | not defined |
| 58 | CH2 | iPr | H | H | H | MeO | 108-111 |
| 59 | CH2 | Me | H | H | H | MeO | liquid |
| 60 | CH2 | —(CH2)4— | | 4'-Me | 8-Me | MeO | 113-116 |
| 61 | CH2 | —(CH2)4— | | 4'-Cl | 6-Cl | MeO | 93-96 |
| 62 | CH2 | —(CH2)4— | | 4'-MeO | 8-Me | MeO | 103-106 |
| 63 | CH2 | —(CH2)4— | | 4'-F | 6-Cl | MeO | liquid |
| 64 | CH2 | Me | Me | H | 7-MeO | MeO | liquid |
| 65 | S | —(CH2)4— | | H | H | O-Na+ | non defined |
| 66 | S | —(CH2)4— | | 4'-Me | H | MeO | liquid |
| 67 | S | Me | Me | H | H | MeO | 75-77 |
| 68 | S | Me | Me | H | H | O-Na+ | not defined |

EXAMPLE 15

Using the appropriate procedures of Examples 1 to 12, the compounds of formula 1 in which $R_4=R_6=R_{10}=H$ and $R_7$ and $R_8$ or $R_9$ and $R_{11}$ together form a single bond, were prepared (table below):

Using the procedures of the intermediate stages of Examples 1 to 4 as appropriate, the intermediate compounds collated in the nonlimiting examples which follow were prepared.

EXAMPLE 17

Intermediate compounds of general formula 4 in which X=O, $R_1$ and $R_2$ form a chain: $-(CH_2)_n-$, $R_7$ and $R_8$ together form a bond, and $R_9$ denotes a hydrogen atom:

| Intermediate compound no. | R3 | R4 | R5 | R6 | n | R11 | M.P. (°C.) |
|---|---|---|---|---|---|---|---|
| 69 | H | H | H | H | 4 | EtO | 84-88 |

-continued

| Intermediate compound no. | R3 | R4 | R5 | R6 | n | R11 | M.P. (°C.) |
|---|---|---|---|---|---|---|---|
| 70 | 4'-Et | H | H | H | 4 | EtO | liquid |
| 71 | H | H | 6-Me | H | 4 | EtO | liquid |
| 72 | H | H | 7-F | H | 4 | MeO | 50–62 |
| 73 | 4'-Me | H | H | H | 4 | EtO | liquid |
| 74 | 3'-F | H | H | H | 4 | EtO | liquid |
| 75 | 4'-MeO | H | H | H | 4 | EtO | liquid |
| 76 | 4'-Cl | H | H | H | 4 | EtO | liquid |
| 77 | 2',3'-CH=CH—CH=CH | | H | H | 4 | EtO | liquid |
| 78 | 3'-Me | 5'-Me | H | H | 4 | EtO | liquid |
| 79 | 4'-F | H | 5-Me | 7-Me | 4 | MeO | liquid |
| 80 | 4'-EtO | H | H | H | 4 | MeO | liquid |
| 81 | 4'-iPrO | H | H | H | 4 | MeO | liquid |
| 82 | 4'-F | H | 6-MeO | H | 4 | MeO | liquid |
| 83 | 4'-CF3 | H | H | H | 4 | MeO | liquid |
| 84 | 4'-PeO | H | H | H | 4 | MeO | liquid |
| 85 | 4'-F | H | 7,8-CH=CH—CH=CH | | 4 | MeO | liquid |
| 86 | 4'-MeS | H | H | H | 4 | MeO | 105–107 |
| 87 | 4'-tBu | H | H | H | 4 | EtO | liquid |
| 88 | 4'-F | H | H | H | 5 | EtO | 95–97 |
| 89 | 4'-F | H | 7-iPrO | H | 4 | MeO | liquid |
| 90 | 4'-Phe | H | H | H | 4 | EtO | liquid |
| 91 | 4'-iPr | H | H | H | 4 | MeO | liquid |

EXAMPLE 18

Intermediate compounds of general formula 4 in which X=O, $R_4=R_5=R_6=R_9=H$ and $R_7$ and $R_8$ form a bond:

| Intermediate compound no. | R1 | R2 | R3 | R11 | M.P. (°C.) |
|---|---|---|---|---|---|
| 92 | H | H | H | EtO | liquid |
| 93 | Me | Me | 4'-F | MeO | 72–79 |
| 94 | H | iPr | 4'-F | EtO | liquid |

EXAMPLE 19

Intermediate compounds of general formula 4 in which X=$CH_2$ or S, $R_4=R_6=R_9=H$, $R_7$ and $R_8$ form a bond and $R_{11}$=methoxy:

| Intermediate compound no. | X | R1 | R2 | R3 | R5 | M.P. (°C.) |
|---|---|---|---|---|---|---|
| 95 | CH2 | —(CH2)4— | | H | H | liquid |
| 96 | CH2 | Me | Me | 4'-F | H | 88–91 |
| 97 | CH2 | Me | Me | H | H | liquid |
| 98 | CH2 | —(CH2)4— | | 4'-F | H | liquid |
| 99 | CH2 | —(CH2)4— | | 4'-Cl | H | liquid |
| 100 | CH2 | Me | Me | 4'-Cl | H | liquid |
| 101 | CH2 | —(CH2)4— | | 3'-F | H | liquid |
| 102 | CH2 | H | H | 4'-F | H | liquid |
| 103 | CH2 | iPr | H | H | H | liquid |
| 104 | CH2 | Me | H | H | H | liquid |
| 105 | CH2 | —(CH2)4— | | 4'-Me | 8-Me | liquid |
| 106 | CH2 | —(CH2)4— | | 4'-Cl | 6-Cl | liquid |
| 107 | CH2 | —(CH2)4— | | 4'-MeO | 8-Me | liquid |
| 108 | CH2 | —(CH2)4— | | 4'-F | 6-Cl | liquid |
| 109 | CH2 | Me | Me | H | 7-MeO | liquid |
| 110 | S | —(CH2)4— | | H | H | liquid |
| 111 | S | —(CH2)4— | | 4'-Me | H | liquid |
| 112 | S | Me | Me | H | H | liquid |

EXAMPLE 20

Intermediate compounds of general formula 2 in which X=O, $R_1$ and $R_2$ form a —$(CH_2)_n$— chain and $R_7$ and $R_8$ form a bond:

| Intermediate compound no. | R3 | R4 | R5 | R6 | n | M.P. (°C.) |
|---|---|---|---|---|---|---|
| 113 | H | H | H | H | 4 | 108–110 |
| 114 | 4'-Et | H | H | H | 4 | 164–166 |
| 115 | H | H | 6-Me | H | 4 | 126–128 |
| 116 | H | H | 7-F | H | 4 | 94–98 |
| 117 | 4'-Me | H | H | H | 4 | 146–148 |
| 118 | 3'-F | H | H | H | 4 | 113–114 |
| 119 | 4'-MeO | H | H | H | 4 | 122–124 |
| 120 | 4'-Cl | H | H | H | 4 | 144–145 |
| 121 | 2',3'-CH=CH—CH=CH— | | H | H | 4 | 138–140 |
| 122 | 3'-Me | 5'-Me | H | H | 4 | 124–126 |
| 123 | 4'-F | H | 5-Me | 7-Me | 4 | 152–156 |
| 124 | 4'-EtO | H | H | H | 4 | 134–136 |
| 125 | 4'-iPrO | H | H | H | 4 | 141–142 |
| 126 | 4'-F | H | 6-MeO | H | 4 | 126–130 |
| 127 | 4'-CF3 | H | H | H | 4 | 172–173 |
| 128 | 4'-PeO | H | H | H | 4 | 68–70 |
| 129 | 4'-F | H | 7,8-CH=CH—CH=CH— | | 4 | 198–201 |
| 130 | 4'-MeS | H | H | H | 4 | 181–183 |
| 131 | 4'-tBu | H | H | H | 4 | 129–131 |
| 132 | 4'-F | H | H | H | 5 | 125–127 |
| 133 | 4'-F | H | 7-iPrO | H | 4 | 134–136 |
| 134 | 4'-Phe | H | H | H | 4 | 147–149 |

-continued

| Intermediate compound no. | R3 | R4 | R5 | R6 | n | M.P. (°C.) |
|---|---|---|---|---|---|---|
| 135 | 4'-iPr | H | H | H | 4 | 172-174 |

EXAMPLE 21

Intermediate compounds of general formula 2 in which $X=CH_2$, O or S, $R_4=R_6=H$ and $R_7$ and $R_8$ together form a bond:

| Intermediate compound no. | X | R1 | R2 | R3 | R5 | M.P. (°C.) |
|---|---|---|---|---|---|---|
| 136 | O | H | H | H | H | 121-123 |
| 137 | O | Me | Me | 4'-F | H | 149-153 |
| 138 | O | H | iPr | 4'-F | H | 159-160 |
| 139 | CH2 | —(CH2)4— | | H | H | 98-103 |
| 140 | CH2 | Me | Me | 4'-F | H | 92-95 |
| 141 | CH2 | Me | Me | H | H | 115-117 |
| 142 | CH2 | —(CH2)4— | | 4'-F | H | — |
| 143 | CH2 | —(CH2)4— | | 4'-Cl | H | 139-141 |
| 144 | CH2 | Me | Me | 4'-Cl | H | 131-133 |
| 145 | CH2 | —(CH2)4— | | 3'-F | H | 100-102 |
| 146 | CH2 | H | H | 4'-F | H | liquid |
| 147 | CH2 | iPr | H | H | H | 110-115 |
| 148 | CH2 | Me | H | H | H | 140-145 |
| 149 | CH2 | —(CH2)4— | | 4'-Me | 8-Me | 122-124 |
| 150 | CH2 | —(CH2)4— | | 4'-Cl | 6-Cl | 150-152 |
| 151 | CH2 | —(CH2)4— | | 4'-MeO | 8-Me | liquid |
| 152 | CH2 | —(CH2)4— | | 4'-F | 6-Cl | 118-120 |
| 153 | CH2 | Me | Me | H | 7-MeO | 112-114 |
| 154 | S | —(CH2)4— | | H | H | 100-111 |
| 155 | S | —(CH2)4— | | 4'-Me | H | 117-119 |
| 156 | S | Me | Me | H | H | 110-112 |

EXAMPLE 22

Intermediate compounds of general formula 6 in which $X=CH_2$ or S, $R_4=R_6=H$.

| Compound No. | X | R1 | R2 | R3 | R5 | M.P. (°C.) |
|---|---|---|---|---|---|---|
| 157 | CH2 | —(CH2)4— | | H | H | 51-56 |
| 158 | CH2 | Me | Me | 4'-F | H | 128-131 |
| 159 | CH2 | Me | Me | H | H | liquid |
| 160 | CH2 | —(CH2)4— | | 4'-F | H | 86-89 |
| 161 | CH2 | —(CH2)4— | | 4'-Cl | H | 90-92 |
| 162 | CH2 | Me | Me | 4'-Cl | H | 153-156 |
| 163 | CH2 | —(CH2)4— | | 3'-F | H | 73-75 |
| 164 | CH2 | H | H | 4'-F | H | 89-90 |
| 165 | CH2 | iPr | H | H | H | liquid |
| 166 | CH2 | Me | H | H | H | liquid |
| 167 | CH2 | —(CH2)4— | | 4'-Me | 8-Me | 135-137 |
| 168 | CH2 | —(CH2)4— | | 4'-Cl | 6-Cl | 147-149 |
| 169 | CH2 | —(CH2)4— | | 4'-MeO | 8-Me | liquid |
| 170 | CH2 | —(CH2)4— | | 4'-F | 6-Cl | 117-119 |
| 171 | CH2 | Me | Me | H | 7-MeO | 71-73 |
| 172 | S | —(CH2)4— | | H | H | 95-97 |
| 173 | S | —(CH2)4— | | 4'-Me | H | 112-114 |
| 174 | S | Me | Me | H | H | 79-81 |

EXAMPLE 23

Intermediate compounds of general formula 5 in which $X=O$ and $R_1$ and $R_2$ form a tetramethylene chain: $—(CH_2)_4—$:

| Intermediate compound no. | R3 | R4 | R5 | R6 | M.P. (°C.) |
|---|---|---|---|---|---|
| 175 | H | H | H | H | 68-71 |
| 176 | 4'-Et | H | H | H | liquid |
| 177 | H | H | 6-Me | H | 66-67 |
| 178 | H | H | 7-F | H | liquid |
| 179 | 4'-Me | H | H | H | 56-58 |
| 180 | 3'-F | H | H | H | 76-78 |
| 181 | 4'-MeO | H | H | H | 58-60 |
| 182 | 4'-Cl | H | H | H | 81-83 |
| 183 | 2',3'-CH=CH—CH=CH— | H | H | H | 121-123 |
| 184 | 3'-Me | 5'Me | H | H | 74-76 |
| 185 | 4'-F | H | 5-Me | 7-Me | liquid |
| 186 | 4'-EtO | H | H | H | liquid |
| 187 | 4'-iPrO | H | H | H | 73-74 |
| 188 | 4'-F | H | 6-MeO | H | 57-61 |
| 189 | 4'-CF3 | H | H | H | 92-94 |
| 190 | 4'-PeO | H | H | H | liquid |
| 191 | 4'-F | H | 7,8-CH=CH—CH=CH— | liquid |
| 192 | 4'-MeS | H | H | H | 66-68 |
| 193 | 4'-tBu | H | H | H | 72-74 |
| 194 | 4'-F | H | 7-iPrO | H | liquid |
| 195 | 4'-Phe | H | H | H | 113-115 |
| 196 | 4'-iPr | H | H | H | liquid |

EXAMPLE 24

Intermediate compounds of general formula 5 in which $R_4=R_6=H$:

| Intermediate compound no. | X | R1 | R2 | R3 | R5 | M.P. (°C.) |
|---|---|---|---|---|---|---|
| 197 | O | —(CH2)5— | | 4'-F | H | 111-114 |
| 198 | O | H | H | H | H | liquid |
| 199 | O | Me | Me | 4'-F | H | 48-50 |
| 200 | O | H | iPr | 4'-F | H | 97-99 |
| 201 | CH2 | —(CH2)4— | | H | H | 135-145* |
| 202 | CH2 | Me | Me | 4'-F | H | 70-73 |
| 203 | CH2 | Me | Me | H | H | liquid |
| 204 | CH2 | —(CH2)4— | | 4'-F | H | liquid |
| 205 | CH2 | —(CH2)4— | | 4'-Cl | H | 53-55 |
| 206 | CH2 | Me | Me | 4'-Cl | H | 92-94 |
| 207 | CH2 | —(CH2)4— | | 3'-F | H | liquid |

-continued

| Intermediate compound no. | X | R1 | R2 | R3 | R5 | M.P. (°C.) |
|---|---|---|---|---|---|---|
| 208 | CH2 | H | H | 4'-F | H | liquid |
| 209 | CH2 | iPr | H | H | H | liquid |
| 210 | CH2 | Me | H | H | H | liquid |
| 211 | CH2 | —(CH2)4— | | 4'-Me | 8-Me | liquid |
| 212 | CH2 | —(CH2)4— | | 4'-Cl | 6-Cl | 127–129 |
| 213 | CH2 | —(CH2)4— | | 4'-MeO | 8-Me | liquid |
| 214 | CH2 | —(CH2)4— | | 4'-F | 6-Cl | 109–111 |
| 215 | CH2 | Me | Me | H | 7-MeO | liquid |
| 216 | S | —(CH2)4— | | H | H | liquid |
| 217 | S | —(CH2)4— | | 4'-Me | H | liquid |
| 218 | S | Me | Me | H | H | liquid |

*B1

EXAMPLE 25

Intermediate compounds of general formula 9 in which $X=S$ and $R_4=R_6=H$:

| Intermediate compound no. | R1 | R2 | R3 | R5 | M.P. (°C.) |
|---|---|---|---|---|---|
| 219 | —(CH2)4— | | H | H | liquid |
| 220 | —(CH2)4— | | 4'-Me | H | 125–126 |
| 221 | Me | Me | H | H | liquid |

EXAMPLE 26

Intermediate compounds of general formula 8 in which $X=S$, $R_4=R_6=H$, $R=C_2H_5$:

| Intermediate compound no. | R1 | R2 | R3 | R5 | M.P. (°C.) |
|---|---|---|---|---|---|
| 222 | —(CH2)4— | | H | H | 126–129 |
| 223 | —(CH2)4— | | 4'-Me | H | 106–107 |
| 224 | Me | Me | H | H | 125–127 |

ANALYTICAL DATA

| Compound No. | | C | H | F | N | Na | Cl | S |
|---|---|---|---|---|---|---|---|---|
| 12 | % Calc. | 74.98 | 7.19 | | | | | |
| | % Fd. | 74.99 | 7.16 | | | | | |
| 13 | % Calc. | 75.60 | 7.61 | | | | | |
| | % Fd. | 75.58 | 7.40 | | | | | |
| 14 | % Calc. | 75.30 | 7.41 | | | | | |
| | % Fd. | 75.04 | 7.18 | | | | | |
| 15 | % Calc. | 71.66 | 6.46 | 4.20 | | | | |
| | % Fd. | 71.87 | 6.31 | 4.20 | | | | |
| 16 | % Calc. | 75.30 | 7.41 | | | | | |
| | % Fd. | 75.27 | 7.61 | | | | | |
| 17 | % Calc. | 72.08 | 6.70 | 4.07 | | | | |
| | % Fd. | 72.04 | 6.66 | 3.99 | | | | |
| 18 | % Calc. | 72.78 | 7.10 | | | | | |
| | % Fd. | 73.00 | 6.90 | | | | | |
| 19 | % Calc. | 69.63 | 6.47 | | | | | 7.34 |
| | % Fd. | 69.72 | 6.51 | | | | | 7.44 |
| 20 | % Calc. | 77.08 | 6.87 | | | | | |
| | % Fd. | 76.90 | 6.92 | | | | | |
| 21 | % Calc.* | 74.20 | 7.68 | | | | | |
| | % Fd. | 74.45 | 7.65 | | | | | |
| 22 | % Calc. | 72.48 | 6.92 | 3.95 | | | | |
| | % Fd. | 72.72 | 6.91 | 3.94 | | | | |
| 23 | % Calc. | 72.78 | 7.16 | | | | | |
| | % Fd. | 72.51 | 7.11 | | | | | |
| 24 | % Calc. | 73.15 | 7.37 | | | | | |
| | % Fd. | 73.41 | 7.20 | | | | | |
| 25 | % Calc. | 69.69 | 6.47 | 3.94 | | | | |
| | % Fd. | 69.81 | 6.49 | 4.17 | | | | |
| 26 | % Calc. | 66.92 | 5.82 | 11.34 | | | | |
| | % Fd. | 66.96 | 5.94 | 11.48 | | | | |

*Calculated with ½ molecule of water.

| Compound No. | | C | H | F | N | Na | Cl | S |
|---|---|---|---|---|---|---|---|---|
| 27 | % Calc. | 73.82 | 7.74 | | | | | |
| | % Fd. | 74.10 | 7.73 | | | | | |
| 28 | % Calc. | 74.09 | 6.22 | 3.78 | | | | |
| | % Fd. | 73.95 | 6.35 | 3.78 | | | | |
| 29 | % Calc. | 69.97 | 6.71 | | | | | 6.67 |
| | % Fd. | 70.04 | 6.77 | | | | | 6.79 |
| 30 | % Calc. | 76.16 | 7.99 | | | | | |
| | % Fd. | 76.21 | 7.94 | | | | | |
| 31 | % Calc. | 72.48 | 6.92 | 3.95 | | | | |
| | % Fd. | 72.23 | 6.99 | 3.86 | | | | |
| 32 | % Calc. | 70.57 | 6.91 | 3.72 | | | | |
| | % Fd. | 70.70 | 6.82 | 3.70 | | | | |
| 33 | % Calc. | 71.21 | 6.67 | 4.33 | 3.19 | | | |
| | % Fd. | 71.03 | 6.47 | 4.26 | 3.04 | | | |
| 34 | % Calc. | 72.63 | 7.15 | 3.96 | 2.92 | | | |
| | % Fd. | 72.37 | 7.04 | 3.87 | 2.79 | | | |
| 35 | % Calc. | 78.66 | 7.15 | | 2.55 | | | |
| | % Fd. | 78.47 | 7.10 | | 2.49 | | | |
| 36 | % Calc. | 73.96 | 7.37 | 3.66 | 2.70 | | | |
| | % Fd. | 73.70 | 7.46 | 3.76 | 2.64 | | | |

-continued

| | | C | H | F | N | Na | Cl | S |
|---|---|---|---|---|---|---|---|---|
| 37 | % Calc. | 75.12 | 6.49 | 3.60 | 2.65 | | | |
| | % Fd. | 74.83 | 6.67 | 3.58 | 2.59 | | | |
| 38 | % Calc.* | 70.13 | 6.73 | | | 4.79 | | |
| | % Fd. | 70.00 | 6.78 | | | 5.05 | | |
| 40 | % Calc.* | 70.57 | 6.94 | | | 4.66 | | |
| | % Fd. | 70.73 | 6.82 | | | 4.71 | | |
| 43 | % Calc. | 73.08 | 6.64 | | | | | |
| | % Fd. | 72.84 | 6.60 | | | | | |

*Calculated with ½ molecule of water

| Compound No. | | C | H | F | N | Na | Cl | S |
|---|---|---|---|---|---|---|---|---|
| 44 | % Calc. | 70.41 | 6.38 | 4.45 | | | | |
| | % Fd. | 70.23 | 6.25 | 4.42 | | | | |
| 45 | % Calc. | 71.35 | 6.87 | 4.18 | | | | |
| | % Fd. | 70.90 | 6.92 | 4.05 | | | | |
| 46 | % Calc. | 77.59 | 6.51 | | | | | |
| | % Fd. | 77.55 | 6.52 | | | | | |
| 47 | % Calc. | 71.99 | 6.04 | 4.22 | | | | |
| | % Fd. | 72.10 | 6.15 | 4.18 | | | | |
| 48 | % Calc. | 78.30 | 7.46 | | | | | |
| | % Fd. | 78.40 | 7.30 | | | | | |
| 49 | % Calc. | 73.44 | 6.16 | | | | | 8.17 |
| | % Fd. | 73.75 | 6.05 | | | | | 8.18 |
| 50 | % Calc. | 77.75 | 7.46 | | | | | |
| | % Fd. | 77.86 | 7.30 | | | | | |
| 51 | % Calc. | 73.56 | 6.89 | 4.48 | | | | |
| | % Fd. | 73.41 | 6.89 | 4.25 | | | | |
| 52 | % Calc. | 76.82 | 7.44 | | | | | |
| | % Fd. | 76.57 | 7.43 | | | | | |
| 53 | % Calc. | 74.64 | 6.93 | 4.22 | | | | |
| | % Fd. | 74.61 | 7.07 | 4.20 | | | | |
| 54 | % Calc. | 72.01 | 6.69 | | | | 7.59 | |
| | % Fd. | 72.01 | 6.54 | | | | 7.64 | |
| 55 | % Calc.* | 69.40 | 6.72 | | | | 7.88 | |
| | % Fd. | 69.24 | 6.55 | | | | 7.88 | |
| 56 | % Calc. | 74.64 | 6.93 | 4.22 | | | | |
| | % Fd. | 74.36 | 7.19 | 4.13 | | | | |
| 57 | % Calc.* | 66.82 | 5.61 | 4.60 | | | | |
| | % Fd. | 66.99 | 5.58 | 4.45 | | | | |
| 58 | % Calc. | 77.11 | 7.67 | | | | | |
| | % Fd. | 77.11 | 7.58 | | | | | |
| 59 | % Calc. | 76.50 | 7.19 | | | | | |
| | % Fd. | 76.72 | 7.25 | | | | | |
| 60 | % Calc. | 78.23 | 7.88 | | | | | |
| | % Fd. | 78.42 | 7.80 | | | | | |

*Calculated with ½ molecule of water

| Compound NO. | | C | H | F | N | Na | Cl | S |
|---|---|---|---|---|---|---|---|---|
| 61 | % Calc. | 67.07 | 6.03 | | | | 14.14 | |
| | % Fd. | 66.90 | 5.83 | | | | 14.04 | |
| 62 | % Calc. | 75.60 | 7.61 | | | | | |
| | % Fd. | 75.90 | 7.45 | | | | | |
| 63 | % Calc. | 69.34 | 6.23 | 3.92 | | | 7.31 | |
| | % Fd. | 69.11 | 6.15 | 4.16 | | | 7.16 | |
| 64 | % Calc.* | 73.29 | 7.44 | | | | | |
| | % Fd. | 73.25 | 7.57 | | | | | |
| 65 | % Calc.° | 71.97 | 6.71 | | | | | 7.12 |
| | % Fd. | 71.76 | 6.89 | | | | | 7.05 |
| 66 | % Calc. | 72.38 | 6.94 | | | | | 6.90 |
| | % Fd. | 72.42 | 6.66 | | | | | 6.92 |
| 67 | % Calc. | 70.73 | 6.65 | | | | | 7.55 |
| | % Fd. | 70.38 | 6.77 | | | | | 7.33 |
| 68 | % Calc.** | 65.96 | 5.88 | | | 5.26 | | 7.34 |
| | % Fd. | 65.89 | 6.10 | | | 5.16 | | 7.19 |

*Calculated with ¼ molecule of water
°Analysis of the corresponding methyl ester
**Calculated with ¾ molecule of water

We claim:
1. A compound formula 1,

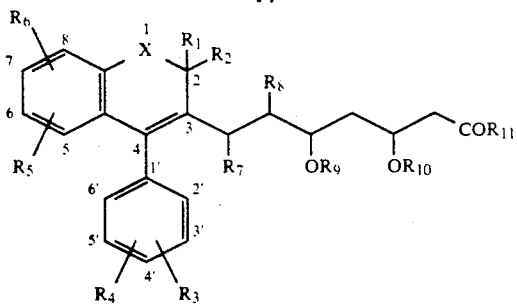

in which X denotes a —CH$_2$— methylene chain link; R$_1$ and R$_2$, which are identical or different, denote hydrogen atoms or alkyl radicals containing 1 to 3 carbon atoms; R$_1$ and R$_2$ may also together form a —(CH$_2$)$_n$— alkylene in which n is 4 or 5, optionally, substituted symmetrically by one or two alkyl radicals containing 1 to 3 carbon atoms; R$_3$ and R$_4$, which may be identical or different, denote hydrogen, fluorine, chlorine or bromine atoms, CF$_3$ radicals, N,N-dialkylamino containing 1 to 3 carbon atoms, alkyl containing 1 to 4 carbon atoms, alkoxy containing 1 to 5 carbon atoms, phenyl optionally substituted by at most two substituents which are identical or different and denote C$_{1-3}$ alkyl radicals or fluorine or chlorine atoms, it being understood that when one of the substituents R$_3$ and R$_4$ denotes a CF$_3$, N,N-dialkyamino, phenyl or substituted phenyl radical, it is present on the 3', 4' or 5' vertex and the other substituent denotes a hydrogen atom; R$_5$ and R$_6$, which may be identical or different, denote hydrogen, fluorine, chlorine or bromine atoms or the radicals: CF$_3$, C$_{1-3}$ alkyl, C$_{1-3}$ alkoxy or phenyl, optionally substituted by one or two C$_{1-3}$ alkyl radicals, C$_{1-3}$ alkoxy or fluorine or chlorine atoms, on condition that when one of the substituents R$_5$ and R$_6$ denotes CF$_3$, phenyl or substituted phenyl radicals, it is present on the vertex 6 or 7 and the other denotes a hydrogen atom; the substituents R$_3$ and R$_4$ or R$_6$ may also together form, on condition of being on two contiguous vertices, the diradicals of formulae: —CH=CH—CH=CH—, —(CH$_2$)$_m$— or —O(CH$_2$)$_p$O—, in which m may be equal to 3 or 4 and p to 1 to 2, it being understood that when R$_3$ and R$_4$ or R$_5$ and R$_6$ denote the diradical —O(CH$_2$)$_p$O—, the latter is linked to the vertices 3' and 4' and 5' or 6 and 7; each of the substituents R$_7$ and R$_8$ denotes a hydrogen atom or, together with the existing C—C bond they form a double bond of trans (E) geometry; each of the substituents R$_9$ and R$_{10}$ denotes a hydrogen atom or together they form a dialkylmethylene residue containing 1 to 3 carbon atoms, R$_{11}$ denoting, with the CO group to which it is bonded, a free acid, ester, amide or acid salt functional group or forming a δ-lactone ring with R$_9$.

2. Compound according to claim 1, characterized in that R$_{11}$ denotes a hydroxyl radical, alkoxy containing 1 to 4 carbon atoms, benzyloxy, alkylamino or N,N-dialkyl-amino containing 1 to 3 carbon atoms, imino containing 4 to 6 carbon atoms, amino or benzylamino or —O$^-$M$^+$ where M$^+$ denotes a pharmaceutically acceptable cation, or R$_{11}$ forms a single bond with R$_9$.

3. Compound according to claim 1, in the formula of which each of the substituents R$_1$ and R$_2$ denotes a methyl group or together they form a tetramethylene chain, R$_3$ and R$_4$ or R$_5$ and R$_6$, which may be identical or different, denote hydrogen, fluorine or chlorine atoms, methyl or ethyl, methoxy, methylthio, phenyl, 4-fluorophenyl, 4-methylphenyl or 4-methoxyphenyl radicals or together form the diradicals: diethylene: —CH=CH—CH=CH, tetramethylene: —(CH$_2$)$_4$— or methylenedioxy: —O(CH$_2$)O—.

4. Compound according to claim 1, characterized in that
(A) each of R$_1$ and R$_2$ denotes a methyl radical or together they form a —(CH$_2$)$_4$— tetramethylene chain, only one of the radicals R$_3$ and R$_4$ or R$_5$ and R$_6$ denotes a hydrogen atom, R$_7$ and R$_8$ together form a bond and each of R$_9$ and R$_{10}$ denotes a hydrogen atom, or
(B) R$_1$, R$_2$, R$_7$, R$_8$, R$_9$ and R$_{10}$ have the meanings given immediately above in (A), one of the substituents R$_3$ and R$_4$ denotes a hydrogen atom and the other a fluorine atom, and only one of the substituents R$_5$ and R$_6$ denotes a hydrogen atom, or
(C) R$_1$, R$_2$, R$_7$, R$_8$, R$_9$ and R$_{10}$ have the meanings which have just been defined above in (A), one of the substituents R$_3$ and R$_4$ is a hydrogen atom and the other denotes a fluorine atom, and each of the two substituents R$_5$ and R$_6$ denotes a hydrogen atom, or
(D) R$_1$, R$_2$, R$_7$, R$_8$, R$_9$ and R$_{10}$ have the particular meanings defined in (A), the two substituents R$_3$ and R$_4$ are hydrogen atoms and only one of the radicals R$_5$ and R$_6$ denotes a hydrogen atom, or
(E) R$_3$, R$_4$, R$_5$, R$_6$, R$_7$, R$_8$, R$_9$ and R$_{10}$ have the meanings above in (C) and R$_1$ and R$_2$ together form a —(CH$_2$)$_4$— tetramethylene chain, or
(F) R$_1$, R$_2$, R$_7$, R$_8$, R$_9$ and R$_{10}$ have the meanings shown immediately above in (E) and each of the substituents R$_3$, R$_4$, R$_5$ and R$_6$ denotes a hydrogen atom.

5. The compound (+,−)methyl 6E-erythro-7-(1,2-dihydro-2,2-dimethyl-4-phenyl-3-naphthyl)-3,5-dihydroxyhept-6-enoate, in accordance with claim 1.

6. Hypocholesterolaemiant or antiatheroschlerous composition comprising a compound according to claim 1, in free acid, ester, amide, salt or δ-lactone form, and a pharmaceutically acceptable excipient.

7. Antithrombotic composition comprising a compound according to claim 1, in free acid, ester, amide, salt or δ-lactone form, and a pharmaceutically acceptable excipient.

8. Antifungal composition comprising a compound according to claim 1, in free acid, ester, amide, salt or δ-lactone form, and a pharmaceutically acceptable excipient.

9. Pharmaceutical composition comprising at least one compound of formula 1 as defined in claim 1, mixed with a pharmaceutically acceptable excipient.

10. Pharmaceutical composition according to claim 9, in dose unit form in which each dose unit contains from 1 to 500 mg of active principles mixed a pharmaceutically acceptable excipient.

11. Method of use of a compound of formula 1 as defined in claim 1, in the treatment of cardiovascular disorders, thrombotic symptoms of diabetes, atherosclerosis and hyperlipoproteinemies, and in anti mycotic treatment, comprising administering to a patient in need of such a treatment a pharmaceutically effective amount thereof.

12. A compound according to claim 1 wherein R$_1$ and R$_2$ form a —(CH$_2$)$_n$-chain, R$_7$ and R$_8$ together form a single bond, each of R$_9$ and R$_{10}$ is hydrogen, and n is 4.

13. A compound according to claim 1 wherein R$_1$ and R$_2$ together form a —(CH$_2$)$_n$-alkylene chain in which n is 4 or 5 optionally substituted by one or two alkyl radicals containing 1 to 3 carbon atoms.

14. A compound of the formula:

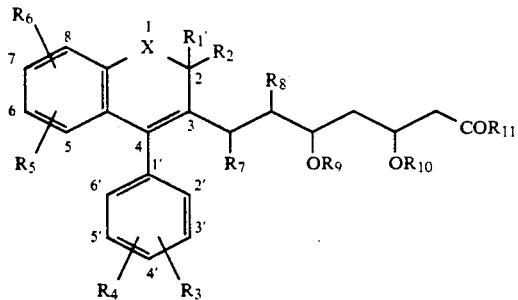

in which X denotes —$CH_2$—; $R_1$ and $R_2$, which are identical or different, denote hydrogen atoms or alkyl radicals containing 1 to 3 carbon atoms; $R_1$ and $R_2$ may also together form a —$(CH_2)_n$— alkylene chain in which the number of n chain links may be equal to 4 or 5 and, if appropriate, substituted symmetrically by one or two alkyl radicals containing 1 to 3 carbon atoms; $R_3$ and $R_4$, which may be identical or different, denote hydrogen, fluorine, chlorine or bromine atoms, $CF_3$ radicals, N,N-dialkylamino containing 1 to 3 carbon atoms, alkyl containing 1 to 4 carbon atoms, alkoxy containing 1 to 5 carbon atoms, phenyl optionally substituted by at most two substituents which may be identical or different and may denote $C_{1-3}$ alkyl radicals or fluorine or chlorine atoms, it being understood that when one of the substituents $R_3$ and $R_4$ denotes a $CF_3$, N,N-dialkyamino, phenyl or substituted phenyl radical, it is present on the 3', 4' or 5' vertices and the other substituent denotes a hydrogen atom; $R_5$ and $R_6$, which may be identical or different, denote hydrogen, fluorine, chlorine or bromine atoms or the radicals: $CF_3$, $C_{1-3}$ alkyl, $C_{1-3}$ alkoxy or phenyl, substituted if appropriate by at most two $C_{1-3}$ alkyl radicals, $C_{1-3}$ alkoxy or fluorine or chlorine atoms, on condition that when one of the substituents $R_5$ and $R_6$ denotes $CF_3$, phenyl or substituted phenyl radicals, it is present on the vertices 6 or 7 and the other denotes a hydrogen atom; each of the substituents $R_7$ and $R_8$ denotes a hydrogen atom or, together with the existing C—C bond they form a double bond of trans (E) geometry; each of the substituents $R_9$ and $R_{10}$ denotes a hydrogen atom, $R_{11}$ denoting with the CO group to which it is bonded a free acid, ester, amide or acid salt functional group.

* * * * *